United States Patent
Swank

(10) Patent No.: US 9,817,948 B2
(45) Date of Patent: Nov. 14, 2017

(54) SYSTEM AND METHOD FOR MONITORING ACTIVITIES THROUGH PORTABLE DEVICES

(71) Applicant: Josh Swank, Peoria, IL (US)

(72) Inventor: Josh Swank, Peoria, IL (US)

(*) Notice: Subject to any disclaimer, the term of this patent is extended or adjusted under 35 U.S.C. 154(b) by 0 days.

(21) Appl. No.: 15/154,228

(22) Filed: May 13, 2016

(65) Prior Publication Data

US 2016/0335410 A1    Nov. 17, 2016

Related U.S. Application Data

(60) Provisional application No. 62/161,975, filed on May 15, 2015.

(51) Int. Cl.
*H04M 11/04* (2006.01)
*G06F 19/00* (2011.01)
(Continued)

(52) U.S. Cl.
CPC ...... *G06F 19/3418* (2013.01); *H04M 1/7253* (2013.01); *H04M 1/72538* (2013.01);
(Continued)

(58) Field of Classification Search
CPC .......... G06F 19/3418; H04M 1/72575; H04M 1/72538; H04M 1/72572; H04M 1/7253; H04W 8/183
(Continued)

(56) References Cited

U.S. PATENT DOCUMENTS 6,340,928 B1    1/2002  McCurdy
6,509,830 B1    1/2003  Elliott
(Continued)

FOREIGN PATENT DOCUMENTS

JP    2001250183 A    9/2001
JP       4403640 B2    11/2009
(Continued)

OTHER PUBLICATIONS

Bugle—App Store, Fitness—http://www.gobugle.com/, retrieved on May 2, 2016, (2 pages).
(Continued)

*Primary Examiner* — Babar Sarwar
(74) *Attorney, Agent, or Firm* — Leydig, Voit & Mayer, Ltd.

(57) ABSTRACT

A device and system are provided for notifying a user contact of the status of a user of a portable device. The status is determined by the portable device collecting user provided information and device collected information relevant to a user of portable device. The portable device may then transmit the device collected information and the user provided information to a server that in turn performs an analysis on the device collected information and the user provided information to determine whether a triggering event has occurred. If it is determined that a triggering event has occurred, the server will proceed to send a status update regarding the user of the portable device to preset user contacts. The triggering event is determined to have occurred based on preset user conditions and algorithms and artificial intelligence being executed at the server.

25 Claims, 18 Drawing Sheets

(51) Int. Cl.
*H04M 1/725* (2006.01)
*H04W 8/18* (2009.01)

(52) U.S. Cl.
CPC ... *H04M 1/72572* (2013.01); *H04M 1/72575* (2013.01); *H04W 8/183* (2013.01)

(58) Field of Classification Search
USPC ..... 455/404.1–404.2, 410–411, 412.1–414.2, 455/418–420, 41.1–41.2, 456.1–457, 455/552.1, 550.1, 466; 370/259
See application file for complete search history.

(56) References Cited

U.S. PATENT DOCUMENTS

| | | | |
|---|---|---|---|
| 7,224,956 | B1 | 5/2007 | O'Neil |
| 7,251,470 | B2* | 7/2007 | Faucher ............. G08B 21/0211 340/539.12 |
| 7,289,786 | B2 | 10/2007 | Krasner |
| 7,349,705 | B1 | 3/2008 | Holland |
| 7,574,195 | B2 | 8/2009 | Krasner et al. |
| 8,045,532 | B2 | 10/2011 | Thomson et al. |
| 8,045,954 | B2* | 10/2011 | Barbeau ........... G08B 13/19658 340/995.1 |
| 8,264,345 | B2 | 9/2012 | Baron, Sr. et al. |
| 8,538,374 | B1* | 9/2013 | Haimo .................... G01S 19/17 370/259 |
| 8,860,568 | B1 | 10/2014 | Baker |
| 8,862,092 | B2 | 10/2014 | Reitnour |
| 9,438,682 | B2* | 9/2016 | Hornor ................... H04L 67/18 |
| 2003/0218539 | A1* | 11/2003 | Hight ................. G08B 21/0244 340/539.13 |
| 2004/0152441 | A1 | 8/2004 | Wong |
| 2004/0203622 | A1 | 10/2004 | Esque et al. |
| 2005/0064887 | A1 | 3/2005 | Bengtsson et al. |
| 2006/0033615 | A1 | 2/2006 | Nou |
| 2006/0068753 | A1 | 3/2006 | Karpen et al. |
| 2007/0087726 | A1 | 4/2007 | McGary et al. |
| 2007/0136678 | A1 | 6/2007 | Brown et al. |
| 2008/0003975 | A1 | 1/2008 | Kim et al. |
| 2008/0188198 | A1 | 8/2008 | Patel et al. |
| 2008/0227429 | A1* | 9/2008 | Hodgson ........... H04M 1/72538 455/404.2 |
| 2009/0037989 | A1 | 2/2009 | Ruggiero et al. |
| 2009/0100144 | A1 | 4/2009 | Sullivan et al. |
| 2009/0197567 | A1 | 8/2009 | Ogram |
| 2009/0286504 | A1 | 11/2009 | Krasner et al. |
| 2010/0003945 | A1 | 1/2010 | Primo et al. |
| 2010/0003954 | A1 | 1/2010 | Greene et al. |
| 2010/0003958 | A1* | 1/2010 | Ray ....................... G10L 13/043 455/404.2 |
| 2010/0046721 | A1 | 2/2010 | Geldenbott et al. |
| 2011/0151829 | A1* | 6/2011 | Velusamy ................ H04L 51/20 455/404.2 |
| 2012/0007735 | A1* | 1/2012 | Rhyins ................ G08B 21/0269 340/539.13 |
| 2014/0057590 | A1* | 2/2014 | Romero .................. H04W 4/22 455/404.2 |
| 2015/0118988 | A1* | 4/2015 | Shaw ..................... G08B 23/00 455/404.1 |
| 2015/0350860 | A1* | 12/2015 | Wimmer ................. H04W 4/22 455/404.2 |
| 2016/0100303 | A1* | 4/2016 | Kim ....................... H04W 76/02 455/426.1 |

FOREIGN PATENT DOCUMENTS

| | | |
|---|---|---|
| KR | 200501033494 A | 10/2005 |
| KR | 100832124 B1 | 5/2008 |
| WO | WO 0235869 A1 | 5/2002 |
| WO | WO 2011162927 A3 | 12/2011 |

OTHER PUBLICATIONS

Emergency Distress Beacon—App Store, Navigation—https://itunes.apple.com/us/app/emergency-distress-beacon/id288770664?mt=8, retrieved on May 10, 2016, (2 pages).
Emergency Button—Google App Store—https://play.google.com/store/apps/details?id=com.emergency.button&hl=en, retrieved on May 10, 2016, (3 pages).
I Am Safe Global Personal Security—Google App Store—https://play.google.com/store/apps/details?id=com.mobiwhiz.iamsafe.app retrieved on May 10, 2016, (3 pages).
CodeRed SOS Emergency—App Store, Healthcare & Fitness—https://itunes.apple.com/us/app/codered-mobile-alert/id468404991?mt=8, retrieved on May 10, 2016, (4 pages).
ADAiHelp—App Store, Utilities—https://itunes.apple.com/us/app/ihelp-plus-personal-alarm/id537514084?mt=8, retrieved on May 18, 2016, (2 pages).
I'm Being Assaulted—App Store, Utilities—https://itunes.apple.com/cv/app/im-being-assaulted/id355459419?mtΛ8 , retrieved on May 18, 2016, (2 pages).
LifeButton—App Store, Navigation—http://lifebutton24.com/ , retrieved on May 18, 2016, (5 pages).
MyForce—App Store, Lifestyle—http://myforce.com/, retrieved on May 18, 2016, (4 pages).
MyLocation—I am Here—App Store, Navigation—https://itunes.apple.com/us/app/mylocation-free/id465935812?mt=8, retrieved on May 18, 2016, (2 pages).
Panic Button Emergency Locator—App Store, Utilities—https://itunes.apple.com/us/app/panic-button-emergency-locator/id321978452?mt=8, retrieved on May 18, 2016, (2 pages).
Ripcord Personal Security—App Store, Lifestyle—https://itunes.apple.com/us/app/ripcord-personal-security/id383054793?mt=8, retrieved on May 18, 2016, (2 pages).
RU OK—Suicide Prevention App—App Store—Lifestyle, RU OK Personal Security—https://itunes.apple.com/us/app/ruok-osu/id577089492?mt=8, retrieved on May 18, 2016, (2 pages).
Silent Bodyguard—Your Personal Panic Button; App Store, Utilities, Fun At Work, 2 pages, May 10, 2010—http://www.silentbodyguard.com/, retrieved on May 18, 2016, (1 page).
WatchOverMe—App Store—http://www.watchovermeapp.com/, retrieved on May 18, 2016, (10 pages).
Companion—App Store—http://www.companionapp.io/, retrieved on May 18, 2016, (6 pages).
Musketeer—App Store—https://www.getmusketeer.com/ , retrieved on May 18, 2016, (5 pages).
BlueLight—App Store—https://getbluelight.com/, retrieved on May 18, 2016, (4 pages).
bSafe—App Store—http://getbsafe.com/, retrieved on May 18, 2016, (3 pages).
React Mobile—https://reactmobile.com/, retrieved on May 18, 2016, (8 pages).
Mr. Gabriel—App Store—http://www.mistergabriel.com/, retrieved on May 18, 2016, (6 pages).
Road ID—App Store—http://www.roadid.com/ecrumbs, retrieved on May 18, 2016, (3 [pages).
Kitestring web service—https://www.kitestring.io/, , retrieved on May 18, 2016, (2 pages).
OnWatchOnCampus—http://www.onwatchoncampus.com/, retrieved on May 18, 2016, (1 page).
Circle of 6—App—http://www.circleof6app.com/, retrieved on May 18, 2016, (7 pages).
Nirbhaya: Be Fearless—India—Android App—http://www.nirbhaya.mobi/, retrieved on May 18, 2016, (6 pages).
PanIcGuard—UK—iOS & Android App—http://panicgaurd.com/, retrieved on May 18, 2016, retrieved on, May 18, 2016 (1 page).
ADT FindU—South Africa—iOS & Android App—http://adtfindu.co.za/ , retrieved on May 18, 2016, (2 pages).
Wear Safe—Hardware safety solution—http://www.wearsafe.com/, retrieved on May 18, 2016, (11 pages).
Figo—Pet tracking hardware and service—https://figopetinsurance.com/, retrieved on May 18, 2016, (10 pages).
Silent Beacon—App Store—https://itunes.apple.com/us/app/silent-beacon-emergency-alert/id933730960?rnt=8, retrieved on May 18, 2016, (2 pages).

(56) References Cited

OTHER PUBLICATIONS

Safetrekapp—app store—https://www.safetrekapp.com, retrieved on May 18, 2016, (9 pages).
My Guardian Angel app—http://myguardianangelappl.com retrieved on May 18, 2016, (9 pages).

* cited by examiner

FINISH ACTIVITY

If you are done with your activity click the button to finish your activity. If not, make sure you come back to the app before 4:00 pm to finish.

FINISH ACTIVITY

FIG. 7A

SYSTEM AND METHOD FOR MONITORING ACTIVITIES THROUGH PORTABLE DEVICES

CROSS-REFERENCE TO RELATED APPLICATIONS

This patent application claims the benefit of U.S. Provisional Patent Application No. 62/161,975, filed May 15, 2015, which is incorporated by reference.

BACKGROUND OF THE INVENTION

Many people rely on portable communication devices such as smart phones for voice communication and accessing information. These devices can also send and receive text messages, download content from the internet, and interface with various third party software applications. Some communication devices have become portable enough to be worn by a user. For example, some wrist watches now incorporate microprocessors, graphic interfaces, and network connectivity allowing the watch to wirelessly communicate with other devices. Additionally, some other devices incorporate sensors for monitoring an environment surrounding the portable device and/or the user carrying the portable device. As such, the portable device collects a variety of information about the user and the environment of the user.

However, the information collected by the portable device may not always be efficiently used to the benefit of the user. For instance, the user may have certain medical conditions that require health monitoring for a heart condition, or the user may travel frequently and need to update concerned persons regarding their location and status. In the case of the user with the medical condition requiring monitoring, concerned individuals may have to make special phone calls or visits to the user to make sure they are okay. And, in the case of the frequent traveler, the user may have to make phone calls or type out a detailed text message to ensure that any concerned individuals are aware of their location and status. Each of these activities is time consuming and inefficient.

BRIEF SUMMARY OF THE INVENTION

One embodiment of the disclosure provides a portable electronic device including a processor, and a network interface for communicating with a wireless network. The portable device further includes an input device for accepting user provided information from a user of the portable device and one or more sensors for acquiring device collected information of the user of the portable device. The portable device also includes a memory comprising instructions for causing the processor to perform the steps of: collecting at least one of the user provided information and the device collected information; and transmitting the at least one of the user provided information and the device collected information to a server for communicating a status to a user contact upon occurrence of a triggering event. In this embodiment, the content of the status is based on at least one of the user provided information and the device collected information.

Another embodiment of the disclosure provides a system for monitoring a user of a portable device. The system includes a portable device associated with the user of the portable device and a server communicatively coupled to the portable device through a wireless network. The portable device includes a processor and a network interface for communicating with the wireless network. The portable device further includes an input device for accepting user provided information of the user of the portable device and one or more sensors for collecting device collected information from the user of the portable device. The portable device also includes a memory comprising instructions for causing the processor to perform the steps of: collecting at least one of the user provided information and the device collected information; and transmitting, by the network interface over the wireless network, at least one of the user provided information and the device collected information to the server.

Yet another embodiment of the disclosure provides a method of reporting a status of a user of a portable device to a user contact. The method receives at least one of user provided information and device collected information of the user collected by at least one of an input device and one or more sensors associated with the portable device. The method also determines, based on the at least one of the user provided information and the device collected information, whether a triggering event has occurred and conditionally communicates the status of the user of the portable device to the user contact when the triggering event has occurred.

BRIEF DESCRIPTION OF THE SEVERAL VIEWS OF THE DRAWING(S)

FIG. 7A illustrates a notification on an example graphic interface display associated with the Going-Out mode according to one embodiment;

DETAILED DESCRIPTION OF THE INVENTION

Many people rely on portable communication devices such as wearable devices and smart phones for voice communication and accessing information. These devices can also send and receive text messages, download content from the internet, and interface with various third party software applications. Some communication devices have become portable enough to be worn by a user. For example, some wrist watches now incorporate microprocessors, graphic interfaces, and network connectivity allowing the watch to wirelessly communicate with other devices, directly or through direct communication to a wireless network. Additionally, some devices incorporate sensors for monitoring an environment surrounding the portable device and/or the wearable device. As such, the portable device collects a variety of information about the user and the environment of the user.

However, the information collected by the portable device may not always be efficiently used to the benefit of the user. For instance, the user may have certain medical conditions that require health monitoring for a heart condition, or the user may travel frequently and need to update concerned persons regarding their location and status. In the case of the user with the medical condition requiring monitoring, concerned individuals may have to make special phone calls or visits to the user to make sure they are okay. And, in the case of the frequent traveler, the user may have to make phone calls or type out a detailed text message to ensure that any concerned individuals are aware of their location and status. Each of these activities is time consuming and inefficient.

To increase the efficiency at which information about a user of the portable device is shared with individuals concerned with the user's well being or safety, the information collected by the portable device can be shared with these concerned individuals such that specialized messages or visits are not needed. In certain embodiments, the portable device associated with the user is configured with an application that will collect information about the user and provide it to a server hosting a service that determines when to contact the concerned individuals based on the information collected from the portable device. The contact initiated by the server may report a variety of information about the user, such as diagnostic information of the user, location information and general well being. These and other features of the disclosure will now be discussed in relation to the figures.

Figure 1:
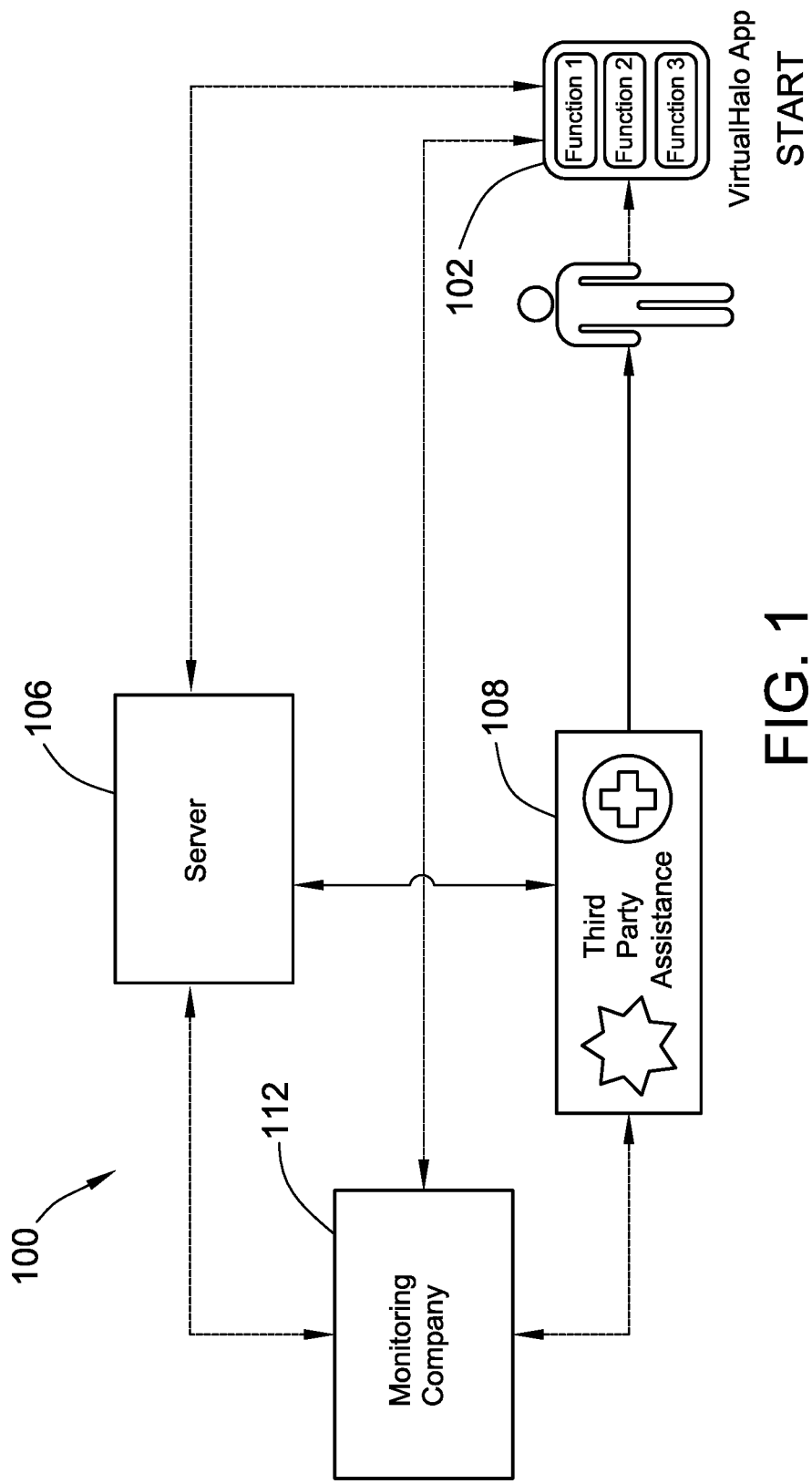
FIG. 1 is a system block diagram in accordance with an embodiment of the disclosure.

FIG. 1 illustrates a system level block diagram, in accordance with an embodiment of the disclosure. The system of FIG. 1 shows a user monitoring and assistance system 100 that includes a user device 102, a server 106, a third party assistance provider 108, and a user monitoring provider 112.

The user device 102 is generally a portable device of a user, such as a mobile, wearable and/or embedded digital device(s), a watch with a computer operating system, a smart phone, a tablet computer, a laptop computer, a personal digital assistant (PDA), a video game console, or any one of a number of additional devices capable of being transported by a user. The user device 102 is capable of executing an application configured to provide user monitoring and assistance. In an embodiment, the user device 102 executing the application configured for user monitoring and assistance is capable of receiving data or information from at least one input device and is configured to communicate with at least one external device using a network interface capable of wireless communication.

In the illustrated embodiment, the user device 102 communicates with both the server 106 and the user monitoring provider 112. In this manner, the user device 102 is able to collect information about the user that can then be transmitted to the server 106 for determination of whether to contact the monitoring provider 112 who can then in turn contact a third party assistance provider 108. Generally, the user provided information collected by the user device falls into one of two categories: (1) user provided information, and (2) device collected information.

User provided information is typically information that is provided by the user to the application via an input device on the user device. For example, the application may prompt the user to provide a status update such as an "I'm OK" indicator, which can then be transmitted to the monitoring provider 112, either directly from the user device or to the server 106 and then to the monitoring provider 112. The user's input indicating the "I'm OK" may be considered user provided information.

Further, the status message may be provided to the monitoring provider 112 is a variety of ways, such as one of a pre-recorded robo-call message, a live phone call, an email, a text message, an application notification message, an operating system notification message, and/or a distress signal. The status message provides the user's status and in certain embodiments, optionally including the location of the user device. In certain embodiments, the location of the user device provided along with the status message could further include a web-link to a map providing the user device location and when the status update was provided, which would constitute device collected information.

Device collected information is typically information collected by various sensors and systems residing on or associated with the user device. For example, the user device 102 may be configured to receive location information with the use of a Global Positioning System (GPS) receiver and transmit the location information to a server 106. Further examples of available sensors are a water sensor, thermometer, accelerometer, light sensor, barometer, altimeter, an image sensor and a microphone. The image sensor and the microphone are respectively capable of capturing image data and audio signals in the vicinity of the user device 102. Other examples of sensors included in the user device 102 are sensors for collecting vital sign information from the user such as a heart rate, blood pressure or blood sugar (including a blood glucose level). The above described sensors and systems are not meant to be limiting on the types of information that may be collected by the user device.

In certain embodiments, one or more of the user provided information and the device collected information may be transmitted to the server 106. The server 106 receives, collects and reacts to the transmitted information by performing one or more actions. In this regard, the server 106 is configured to analyze parameters based on information related to the user and react according to pre-determined triggering events. For example, in an embodiment, the server 106 may analyze the location information in combination with other parameters, such as the time of day, a preconfigured setting created by the user, and/or input information obtained from other sensors located on or within the user device 102 to determine whether a triggering event has occurred.

In performing the above described functions, the server 106 hosts a service that functions to receive the information from the application for user monitoring and assistance being executed by the user device 102 and utilizes that information to determine whether to send a notification message to a third party. The service hosted by the server 106 is configured to provide this service to a plurality of subscribers who are users of user devices 102 that include the application for user monitoring and assistance. Each of the subscribers has an account with the service such that unique information regarding that particular subscriber can be provided to help determine system functionality, such as when to send certain notification messages and who or what should receive the messages. In this regard, the user can set up triggering events that will trigger status updates to be sent in one of a variety of forms to one or more recipients, for example, monitoring provider 112, based on the user provided information and/or the device collected information received from the user device 102. Additionally, the server 106 may use algorithms and artificial intelligence to analyze the user provided information and the device collected information from the user device 102 to determine the occurrence of a triggering event.

The server 106 is generally configured to communicate with external devices via one or more networks. Such networks may include one or more wireless networks, wired networks, fiber optics networks, and other types of networks through which communication between the server 106 and an external device may be established. In certain embodiments, the server 106 may send/receive data to/from the user device 102, the third party assistance provider 108, the user monitoring provider 112, or any combination thereof. The parameter information received by the server 106 generally pertains to the user provided information and the device collected information.

In an embodiment, the server 106 is configured to take any number of pre-determined actions based on a particular triggering event. A triggering event is an event that when noticed by the server 106 causes the server 106 to take an action on behalf of the user of the user device 102. Examples of triggering events may include: (1) one of a variety of measured vital signs, such as heart rate, blood pressure or blood sugar, exceed a predetermined threshold; (2) expiration of a time period or a preset time interval has expired; (3) leaving a pre-defined geographic space; and (4) receiving a message from the user device 102 that assistance is needed. In each of these examples, the server 106 would detect the triggering event and proceed to take a specific action in response to the triggering event. The parameters associated with these triggering events may be preset at the server 106 by the user accessing her user account with the service hosted by the server 106. In certain embodiments, this access may be conducted over a web interface with the service.

The third party assistance provider 108 shown in FIG. 1 may be an emergency dispatch service, such as public "911" dispatch or a similar service provided by a private entity or person. The third party assistance provider may also provide non-emergency service. For example, the third party assistance provider may try calling the user or visiting the user. To assist in providing its server, in an embodiment, the third party assistance provider 108 receives the user's last known location from the server 106. The location may be provided either through a status update message or the third party assistance provider 108 may be able to access a user account at the server 106 that stores reported locations of the user device 102.

The user monitoring provider 112 functions as a monitoring service for the user and is configured to receive messages from both the user device 102 and the server 106. In one embodiment, the user monitoring provider 112 is a user contact that has been configured within the service hosted by the server. The user contact receives notification messages from the user device 102 and/or the server 106 related to a status of the user of the user device 102 and based on the user provided information and the device collected information. In another embodiment, the user monitoring provider 112 may be an optional service, such as a service requiring a monthly or annual subscription where employees of the service process the notification messages containing a user status provided from the user device 102 or the server 106. In yet another embodiment, the monitoring provider 112 may include both the subscribed to service and one of a number of user contacts of the user of the user device 102. Based on information preset by the user at the service hosted at the server 106, the various status updates and notification messages can be directed to one or more of the monitoring provider as a subscribed to service or a user contact.

In general, the user monitoring provider 112 receives status messages containing user provided information and or device collected information from the server 106 based on the occurrence of a triggering event. For example, the monitoring provider 112 may be informed when a user travels beyond a certain geographic region, thereby allowing the monitoring provider 112 to take further actions for the safety of the user. In an embodiment, the monitoring provider 112 may cause the server 106 to send notification messages to user contacts, which may include a friend or family member of the user. In other embodiments, the monitoring provider 112 may send notifications to the user device 102. In certain embodiments, the server 106 will send a user contact status message back to the user device 102 once the notification message has been sent to the user contact or monitoring provider 112. The user contact status message can be utilized by the user device 102 to display that the notification message has been sent to the user contact.

In another embodiment, the user monitoring provider 112 is configured to directly receive information from the user device 102, the server system 106, or any combination thereof. The information may include the same type of information used as parameters for the server 106. In an embodiment, the user monitoring provider 112 may provide a service in which a user can contact the user monitoring provider 112 for assistance. For example, in an emergency situation, the user may use a graphic interface of the user device 102 to contact the user monitoring provider 112 for assistance.

As an aside, FIG. 1 does not illustrate the user contacts as being separate from the monitoring provider 112. Rather, FIG. 1 illustrates the single block monitoring provider 112 as representative of both the subscribed to service monitoring provider 112 discussed above and the preset user contacts. FIG. 1 could be illustrated as replacing the monitoring provider 112 with user contacts or user contacts in parallel with the monitoring provider 112 and also in communication with the server 106.

Figure 1A:
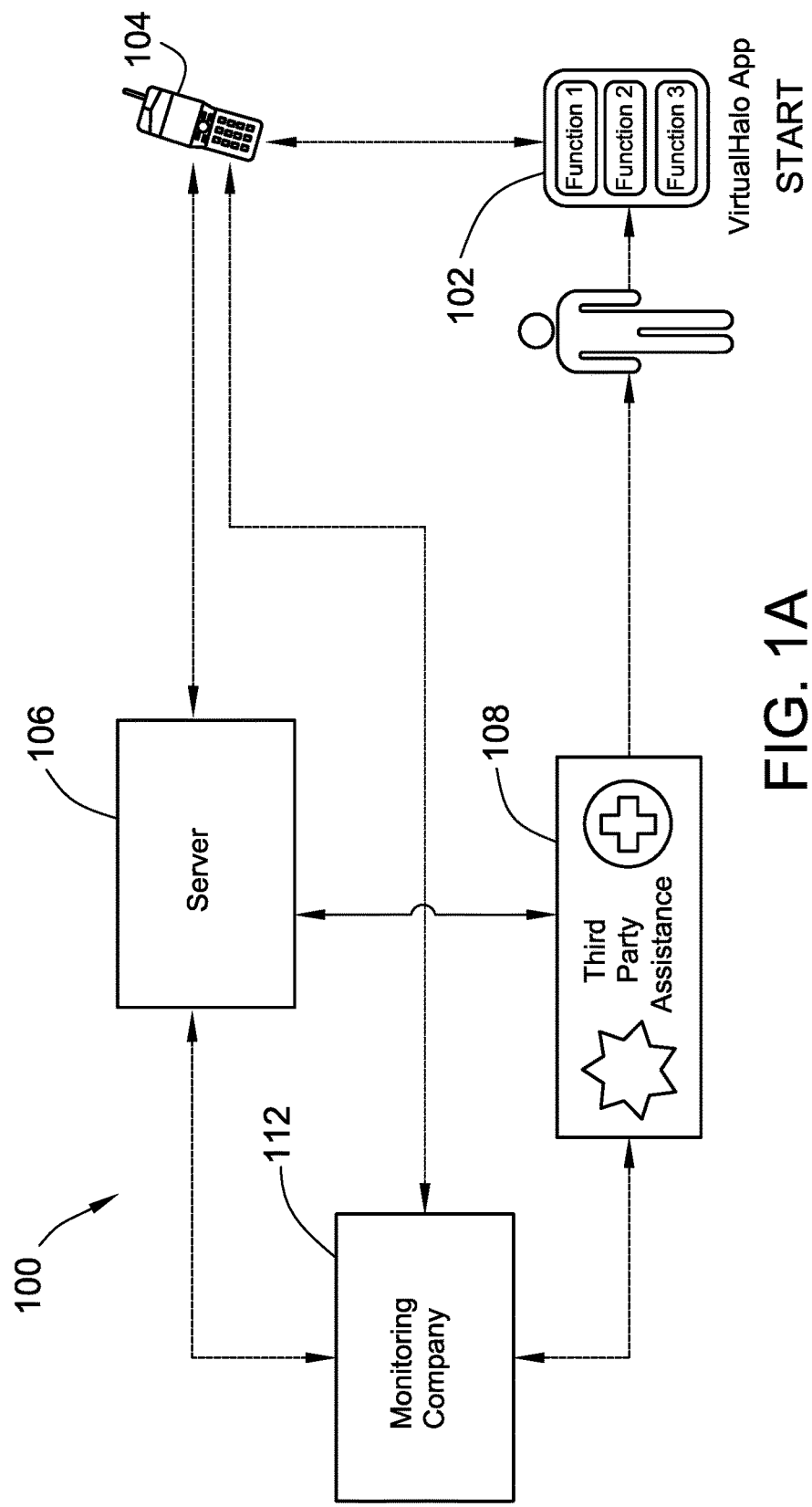
FIG. 1A is a system block diagram in accordance with an embodiment of the disclosure.

FIG. 1 is not intended to limit the environments that may be used. For example, while FIG. 1 shows the user device 102 directly communicating with the server system 106 and also directly communicating with the user monitoring provider 112. Other system configurations are contemplated herein. For example, as illustrated in FIG. 1A, another configuration may involve the user device 102 communicating with a tethered device 104, whereby the tethered device 104 is then configured to communicate with the user monitoring provider 112 and also with the server 106. In FIGS. 1 and 1A, the user device 102 or tethered device 104 is configured for bidirectional communication between the server system 106 and the user monitoring provider 112 such that data is both sent and received from the user device 102 or tethered device 104.

Figure 1B:
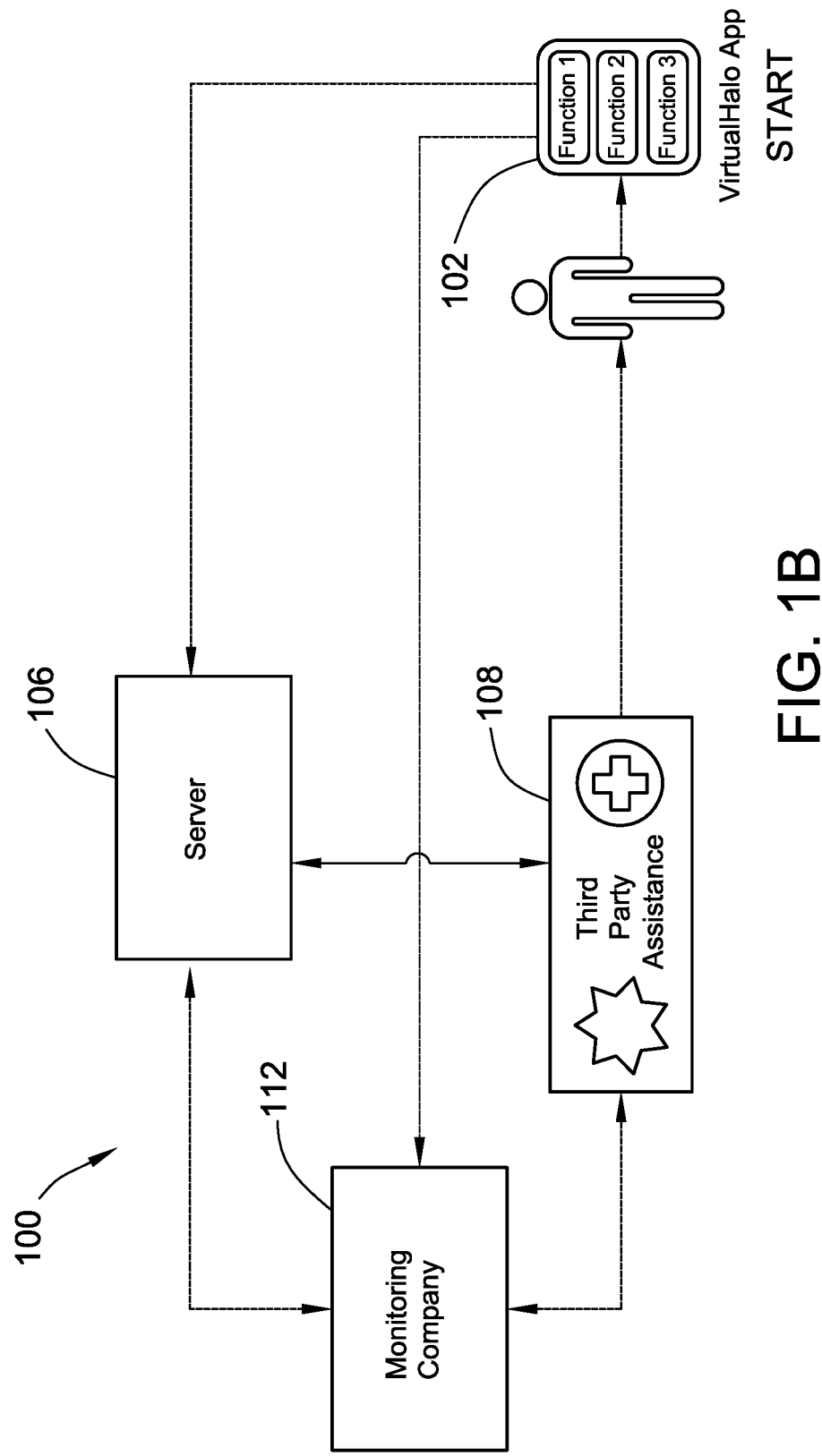
FIG. 1B is a system block diagram in accordance with an embodiment of the disclosure.
Figure 1C:
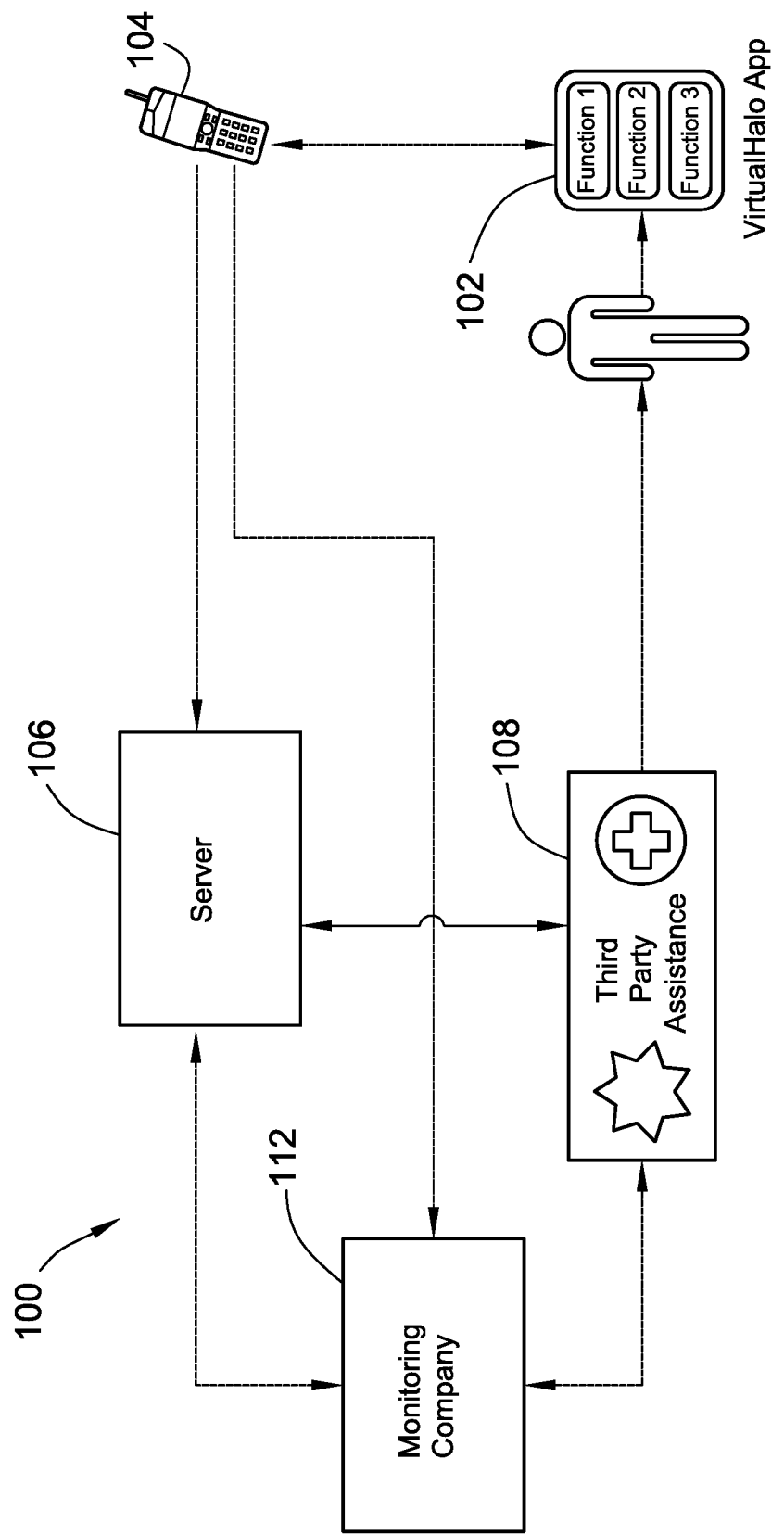
FIG. 1C is a system block diagram in accordance with an embodiment of the disclosure.

In other embodiments, as illustrated in FIGS. 1B and 1C, the user device 102 or tethered device 104 is configured for unidirectional communication with the server system 106 and the user monitoring provider 112. The unidirectional communication configuration limits the user device 102 or tethered device 104 from receiving messages back from the server 106 and user monitoring provider 112. In certain embodiments, the bidirectional communication can be converted to unidirectional communication in situations of poor cellular signal strength, when battery power of the user device 102 or tethered device 104 needs to be conserved, or any other circumstances where unidirectional communication is preferred.

In embodiments including the tethered device 104, as shown in FIG. 1A, the tethered device 104 runs the application for providing user monitoring and assistance and communicates with the user device 102 as needed to transmit messages to and receive messages from other network entities. The tethered device 104 may be a mobile device such as a wearable or embedded digital device(s), a watch with a computer operating system, a smart phone, a tablet computer, a laptop computer, a personal digital assistant (PDA), a video game console, or any one of a number of additional devices capable of displaying content and being transported by a user. In an embodiment, the tethered device is configured with a network interface capable of wireless communication with the user device 102 and a server system 106. In an example embodiment, the user device 102 is a wearable device such as a watch and the tethered device 104 is a smart phone or tablet computer that's configured to send and receive data with the user device 102.

Figure 2:
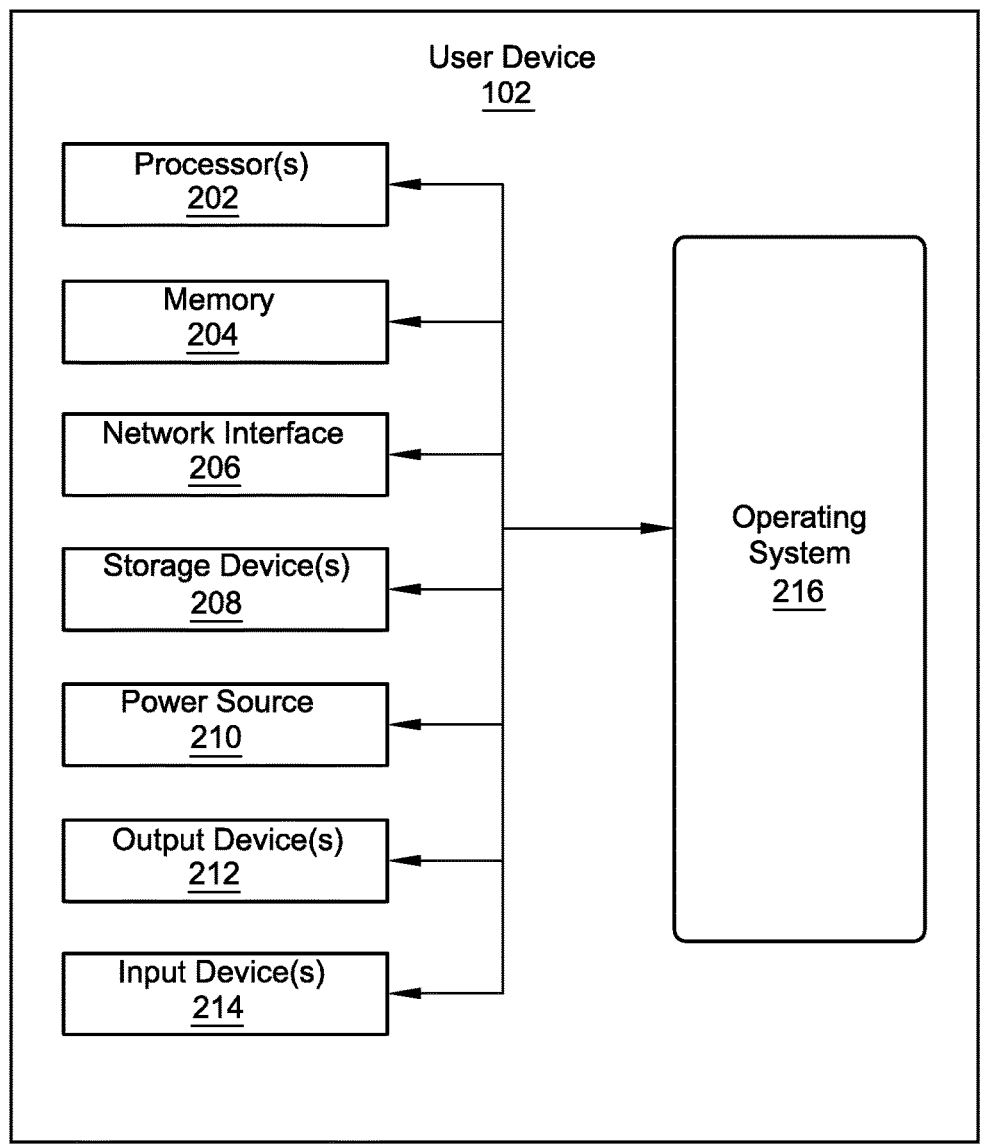
FIG. 2 is a block diagram illustrating components of the portable device shown of FIG. 1, according to one embodiment.

FIG. 2 shows a block diagram of basic functional components included in one or more of the user device 102 and the tethered device 104, depending on the system configuration. While the discussion below with respect to FIG. 2 discusses components of the user device 102, the discussion is equally applicable to the tethered device 104.

Generally, the user device 102 is configured to perform certain steps in order to enact various modes of the application executed by the user device 102. In enacting the various modes, the user device 102 typically collects user provided information and the device collected information, as discussed above. Based on the device collected information and/or the user provided information, the user device 102 will also transmit that user provided information and/or the device collected information to the server 106 for communicating a status to a user contact upon occurrence of a triggering event.

As illustrated in FIG. 2, the user device 102 includes one or more processors 202, a memory 204, a network interface 206, one or more storage devices 208, a power source 210, one or more output devices 212, one or more input devices 214, and an operating system 216. Each of the components including the processor 202, memory 204, network interface 206, storage device 208, power source 210, output device 212, input device 214, and the operating system 216 is interconnected physically, communicatively, and/or operatively for inter-component communications.

The processor 202 is configured to process instructions for execution within user device 102. In an embodiment, processor 202 executes instructions stored in memory 204 or instructions stored in a storage device 208. The memory 204 may be a non-transient, computer-readable storage medium, and configured to store information within user device 102 during operation. In some embodiments, the memory 204 includes a temporary memory, an area for information not to be maintained when the user device 102 is turned off. For example, the temporary memory may include volatile memories such as random access memories (RAM), dynamic random access memories (DRAM), and static random access memories (SRAM). The memory 204 also maintains instructions for execution by the processor 202.

Storage device 208 also includes one or more non-transient computer-readable storage media. The storage device 208 is generally configured to store larger amounts of information than memory 204. In an embodiment, the storage device 208 may further be configured for long-term storage of information. The storage device 208 may include non-volatile storage elements such as magnetic hard discs, optical discs, floppy discs, flash memories, or forms of electrically programmable memories (EPROM) or electrically erasable and programmable (EEPROM) memories.

The user device 102 uses network interface 206 to communicate with external devices using one or more wireless networks, and other types of networks through which a communication with the user device 102 may be established. In the illustrated embodiment of FIG. 1, the network interface 206 of the user device 102 may communicate directly with the server 106 and monitoring company 112, as described above. In another embodiment, illustrated in FIG. 1A, the network interface 206 of the user device 102 communicates directly with the tethered device 104.

The network interface 206 may be an optical transceiver, a radio frequency transceiver, or any other type of device that can send and receive information. Non-limiting examples of network interfaces 206 include near field communication (NFC) interfaces, Bluetooth®, 3G and 4G cellular network interfaces, Satellite-based communication, WiFi®, and USB interfaces.

The user device 102 includes one or more input devices 214. Input devices 214 can be configured to receive input from an environment surrounding a user of from direct interaction with the user. In this regard, many input devices can be characterized as sensors. Examples of input devices may include a touch-sensitive screen, a keyboard, a microphone, and an image sensor. Other input devices 214 may include a proximity sensor, a light sensor, a water sensor, thermometer, altimeter, barometer and an accelerometer. Embodiments may also include input devices 214 configured to track the user device's 102 location, such as using an antenna configured to receive location information from Global Positioning System (GPS) or through use of data networks such as WLAN or WAN to triangulate the user device's 102 position based on a measured signal strength received from at least two access points.

In other embodiments, the input devices 214 may additionally or alternatively include diagnostic sensors configured to gather vital sign, diagnostic and other health-related information from a user. For example, input devices 214 may include a heart rate sensor, a glucose sensor, and a blood pressure sensor. The number and type of sensors is not intended to be limited to any particular quantity or combination.

One or more output devices 212 are also included in user device 102. Output devices 212 are configured to provide output to a user using tactile, audio, and/or video stimuli. Output device 212 may include a liquid crystal display (LCD) screen, a sound card, a video graphics adapter card, or any other type of device for converting a signal into an appropriate form understandable to humans or machines.

The user device 102 includes one or more power sources 210 to provide power to the device. Non-limiting examples of power source 210 include single-use power sources, rechargeable power sources, and/or power sources developed from nickel-cadmium, lithium-ion, solar, or other suitable material.

The user device 102 includes an operating system 216. The operating system 216 controls operations of the components of the user device 102. For example, the operating system 216 facilitates the interaction of the processor(s) 202, the memory 204, the network interface 206, storage device(s) 208, input devices 214, output devices 212, and power source 210. Additionally, the operating system 216 may provide a user interface that provides user access to the application for providing user monitoring and assistance.

Figure 3:
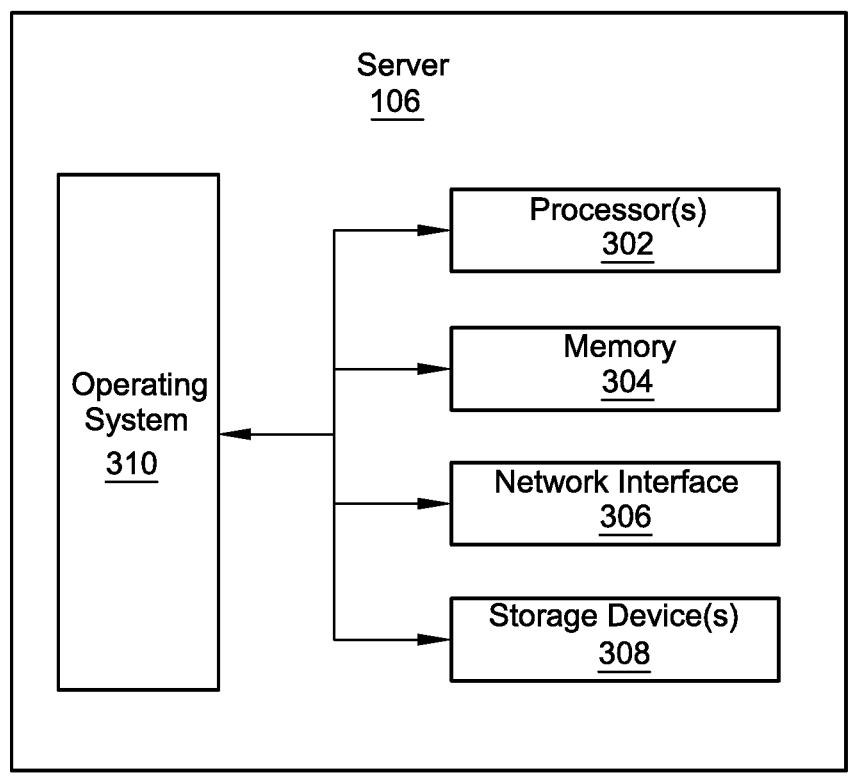
FIG. 3 is a block diagram illustrating functional components of the server shown in FIG. 1, according to one embodiment.

FIG. 3 shows a block diagram of basic functional components for a server 106 according to one aspect of the disclosure. The server 106 is generally configured to send data to and receive data from the user device 102, the tethered device 104, or both. The server 106 is also configured to send data to and receive data from the monitoring provider 112.

Generally, the server 106 is configured to host the service subscribed to by a user of the user device 102. The service enables the server 106 to receive the user provided information and/or device collected information from the user device 102. The service is then configured to determine, based on the user provided information and/or the device collected information, whether a triggering event has occurred. If it is determined that the triggering event has occurred, then the service will cause the server 106 to communicate a status of a user of the user device 102 to a user contact, such as the monitoring provider 112. In certain embodiments, the service may also cause the server 106 to transmit a user contact status message. The user contact status message is a message sent by the server 106 to the user device 102 indicating that the user's status has been provided to the user contact. In certain embodiments, the user device 102, upon receiving the user contact status message, will update the user that the status has been reported to the user contact via an output device on the user device 102.

In FIG. 3, the server 106 is illustrated as a single entity. However, in other embodiments, the server 106 could be implemented as a plurality of servers configured in a server system or as a cloud server.

The server 106 includes one or more processors 302, a memory 304, a network interface 306, one or more storage devices 308 and an operating system 310. In some embodiments, each of the components including the processors 302, a memory 304, a network interface 306, storage device 308, and operating system 310 are interconnected physically, communicatively, and/or operatively for inter-component communications.

As illustrated, processors 302 are configured to implement functionality and/or process instructions for execution within server 106. For example, processors 302 execute instructions stored in memory 304 or instructions stored on storage devices 308. The memory 304, which may be a non-transient, computer-readable storage medium, is configured to store information within server 106 during operation. In some embodiments, memory 304 includes a temporary memory, i.e. an area for information not to be maintained when the server 106 is turned off. Examples of such temporary memory include volatile memories such as random access memories (RAM), dynamic random access memories (DRAM), and static random access memories (SRAM). Memory 304 also maintains program instructions for execution by the processors 302.

Storage devices 308 also include one or more non-transient computer-readable storage media. Storage devices 308 are generally configured to store larger amounts of information than memory 304. Storage devices 308 may further be configured for long-term storage of information. In some examples, storage devices 308 include non-volatile storage elements. Non-limiting examples of non-volatile storage elements include magnetic hard discs, optical discs, floppy discs, flash memories, or forms of electrically programmable memories (EPROM) or electrically erasable and programmable (EEPROM) memories.

The server 106 uses network interface 306 to communicate with external devices via one or more networks. Such networks may include one or more wireless networks, wired networks, fiber optics networks, and other types of networks through which communication between the server 106 and an external device may be established. Network interface 306 may be a network interface card, such as an Ethernet card, an optical transceiver, a radio frequency transceiver, or any other type of device that can send and receive information. The network interface 306 of the server system 106 may be configured to communicate with the user device 102, the tethered device 104, the third party assistance provider 108, the user monitoring provider 112, or any combination thereof, as described above. The network interface 306 may be used for sending notification messages based on triggering events, as described above. The number, content, and type of notifications and the recipients of the notifications are not intended to be limited to any particular configuration.

The server 106 includes an operating system 310. The operating system 310 controls operations of the components of the server 106. For example, the operating system 310 facilitates the interaction of the processor(s) 302, the memory 304, the network interface 306, and storage device(s) 308.

Figure 4:
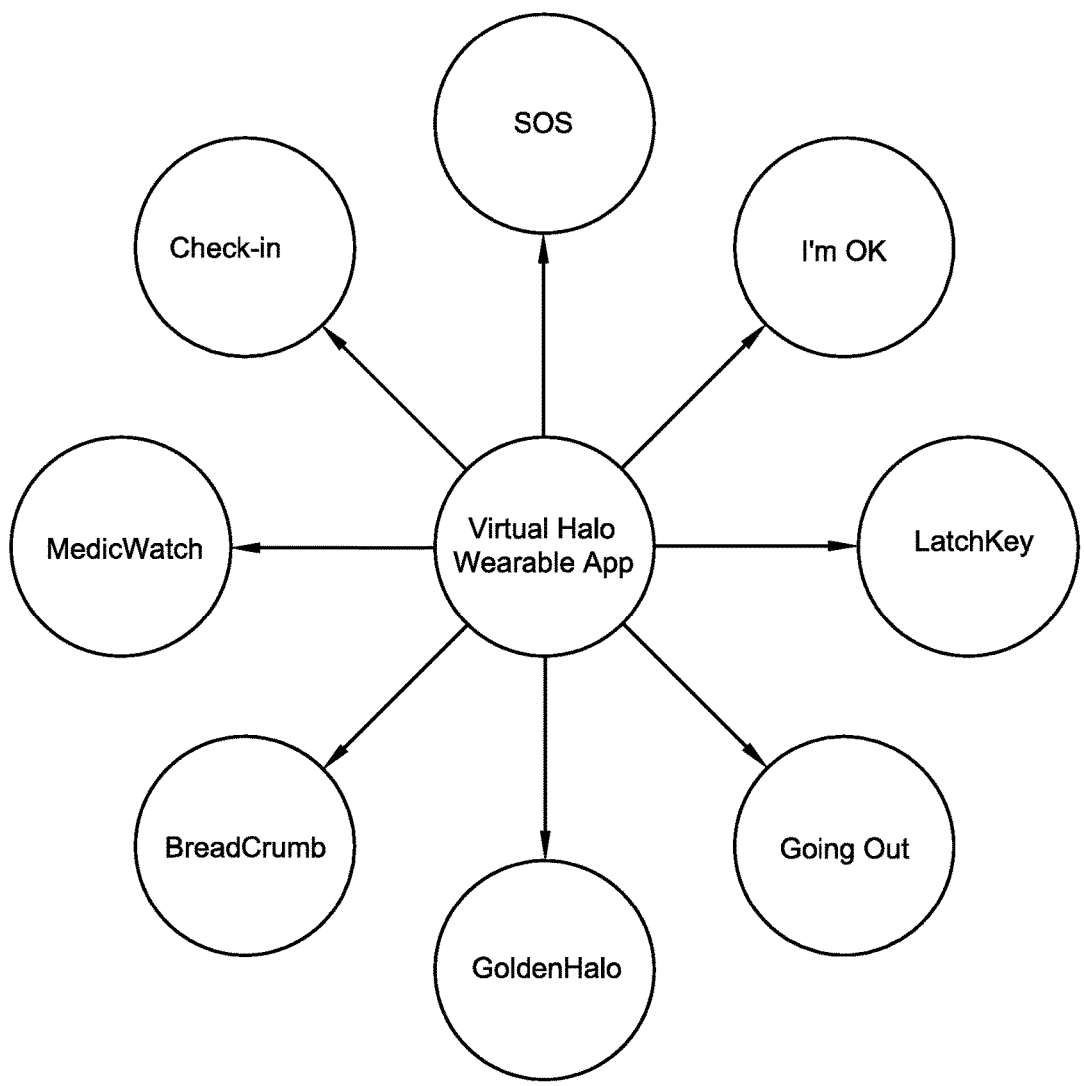
FIG. 4 is a diagram illustrating examples of various modes according to one embodiment.

Turning now to FIG. 4, a non-exhaustive list of various functions or modes that can be performed by embodiments of the systems shown in FIG. 1-1C is provided. The example modes are not intended to be limiting, and various other modes may be performed in accordance with the present disclosure. For readability and convenience, the various modes described below may be referred to as brand or trade names or similar.

In one mode referred to as MedicWatch, the user device is configured to collect various diagnostic and health-related information through at least one input device, and the received information is used as parameter information for at least one triggering event, such as contacting third party assistance or a paramedic. In a second mode, referred to as the SOS mode, a countdown timer is initiated, requiring the user to type a preset personal identification number (PIN) number before expiration of a countdown timer. If the preset PIN number is not entered before the countdown timer expires, then a sequence of notifications may be triggered. In a third mode, referred to as GoingOut, a user can select an activity and an associated time duration, and notification messages may be triggered if the user has not indicated completion of the activity within the time duration. In a fourth mode, referred to as GoldenHalo, a series of notification messages may be triggered depending on a user's location and other device collected information. In a fifth mode, referred to as I'm OK, a series of notifications may be triggered based on user input indicating that assistance is needed. In a sixth mode, referred to as LatchKey, a notification message may be triggered when the user enters or exits a preset geographic area.

In a seventh mode, referred to as Check-In, the user can conveniently send notification messages to at least one preset destination, whereby the notification may include location or a configurable message. In an eighth mode, referred to as Breadcrumb, the user device 102 captures its geographical location and transmits it along with a timestamp to the server 106, where the location and time information may then be accessed by the user or a third party with access to the user's private account information stored on the user device 102 and/or at the server 106.

Medicwatch Mode

Figure 5:
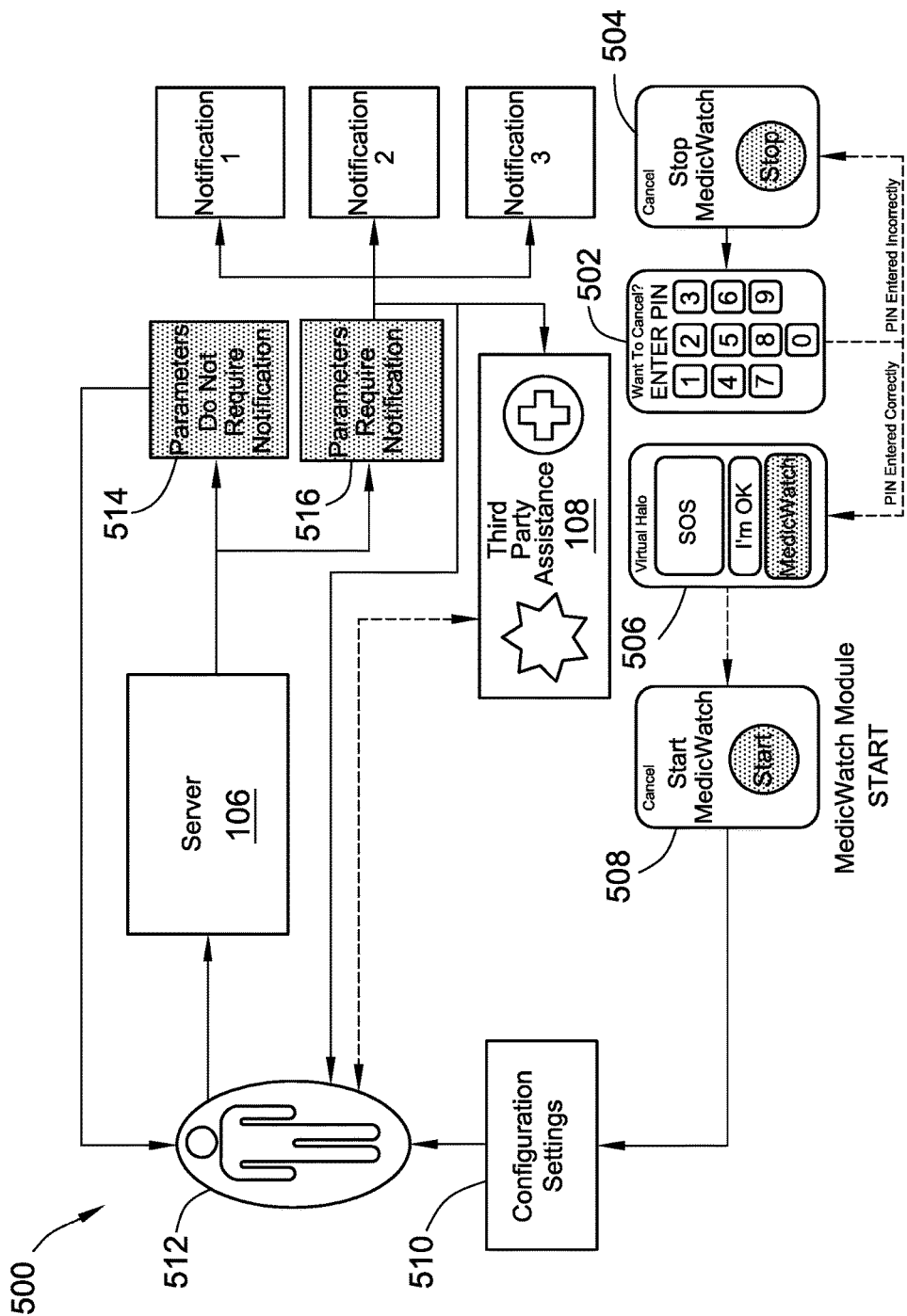
FIG. 5 is a flowchart illustrating the MedicWatch mode according to one embodiment.

FIG. 5 shows a flowchart describing the various sequence steps of the MedicWatch mode. In this mode, the user device is configured to collect various diagnostic and health-related information through at least one input device, and the received information is used as parameter information for at least one triggering event, such as contacting third party assistance or a paramedic. This example mode may be implemented by the user device 102 or in combination with the tethered device 104, and the mode may be performed within various system environments, such as those shown in FIGS. 1-1C.

At step 506, the graphic interface displays the various modes that a user can select from, including the MedicWatch mode.

At step 508, a graphic interface illustrating the MedicWatch start screen is shown. In an embodiment, a touch-sensitive button on the graphic interface permits the user to initiate the mode.

At step 510, the graphic interface display permits the user to adjust configuration settings. In general, configuration of settings is optional after an initial setup procedure. As such, each time the user accesses the MedicWatch mode, providing configuration settings for this mode will not be necessary. The configuration settings generally relate to user provided information and device collected information, and in particular relate to diagnostic or vital sign information of the user. Some non-limiting examples of user provided information relevant to MedicWatch include the user's age, weight, health conditions, allergies, medications, and blood type. Device collected information can include heart rate, blood pressure, blood sugar or blood glucose level, geographic location, motion activity, and any other information that can be obtained through sensors and/or an input device.

During configuration, the user sets various thresholds, such as a maximum and/or minimum blood pressure level, maximum and/or minimum heart rate and maximum and/or minimum blood sugar level. These thresholds are then utilized as triggering events to determine when the server 106 (see FIG. 1) should send a notification message to the monitoring provider 112. The notification message may include certain user provided information and device collected information, such as the user's age, weight, health conditions, allergies, medications, blood type and current location, which may assist any monitoring provider 112 or third party assistance provider 108 in helping the user in case of a medical emergency. The information provided in the notification message may be configured during the user configuration step 510.

The user provided information and device collected information is transmitted to the server 106 and stored at the server 106. In other embodiments, configuration of settings can be accomplished using the tethered device 104 or a web interface accessible through an internet connected device. The user provided information and the device collected information is accessible by the user when they sign into their account at the service provided by the server 106.

At step 512, the MedicWatch mode generally monitors device collected information, and in particular vital sign and diagnostic information, such as heart rate, blood pressure, blood sugar or blood glucose level. This information can be analyzed to determine whether a triggering event has occurred, such as exceeding a threshold set during the configuration step 510. For example, after a user sets a maximum blood pressure threshold at step 510, a triggering event may occur when a blood pressure measurement exceeds that threshold. Triggering events are not limited to any particular combination of user provided and device collected information. In an embodiment shown in FIG. 5, the server 106 (see FIG. 1) receives the user provided and device collected information, and determines whether a triggering event has occurred. In other embodiments, this may be accomplished by the user device 102 or the tethered device 104.

At step 514, the server 106 (see FIG. 1) has determined that a triggering event has not occurred based on the received user provided and device collected information. In absence of a triggering event, the MedicWatch mode continues monitoring as described in step 512. In an embodiment, the MedicWatch mode may terminate monitoring after a preset time or may terminate based on user provided and collected information. The conditions under which the MedicWatch mode may terminate may be set by the user during the configuration step 510.

At step 516, the server 106 (see FIG. 1) has determined a triggering event has occurred. Upon detecting the triggering event, the server 106 is generally configured to initiate at least one notification message. The notification messages may be sent to the user, the third party assistance provider 108, the monitoring provider 112, or any other recipient. In an embodiment, the monitoring provider 112 may send notification to the third party assistance provider 108 or any other recipient in order to have medical assistance provided to the user. Notification messages may vary depending on the triggering event and various combinations of user provided and device collected information. For example, in an embodiment that uses blood pressure as a triggering event, if the user is within a certain geographic zone, one notification message to the user may indicate that medication should be taken. Additional notification messages may be sent to other recipients if the user exits that geographic zone. The content, type, and destination of notification messages may vary based on user provided information and device collected information.

At step 504, the graphic interface includes a stop button, which then engages an authentication, allowing the user to disable the MedicWatch mode.

At step 502, a user authenticates by the user device 102. In certain embodiments, the authentication can be accomplished by entering a personal identification number (PIN) on a touch-sensitive graphic interface of the user device 102. Authentication may be performed by any number of methods, such as biometric, voice, image or password. Successful authentication disables the MedicWatch mode.

At step 506, successful authentication has occurred, disabling the MedicWatch mode. The graphic interface displays the various modes that a user can select from, including the MedicWatch mode. However, if authentication is unsuccessful, then the user device 102 will continue operating the MedicWatch mode.

SOS Mode

Figure 6:
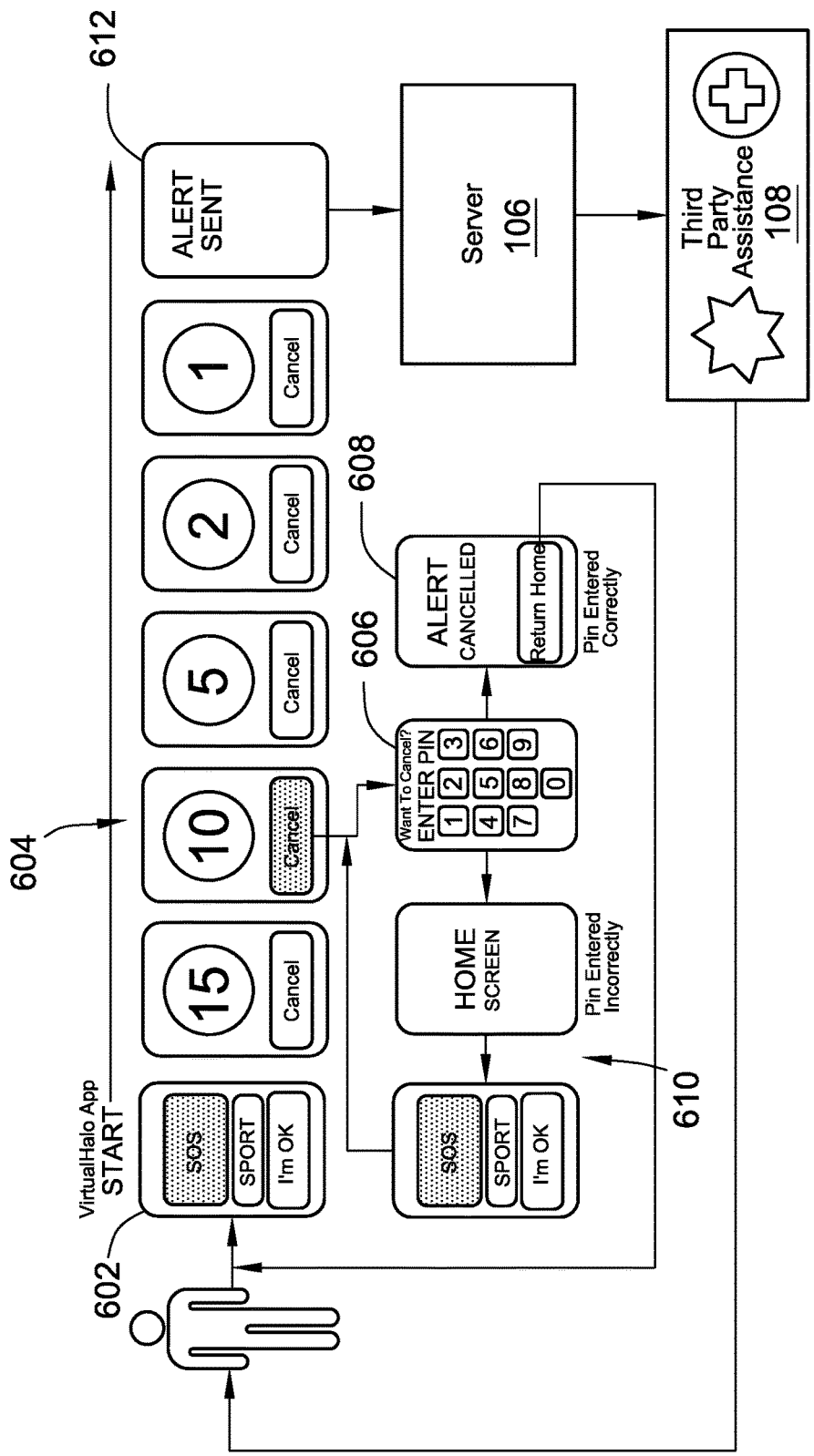
FIG. 6 is a flowchart illustrating the SOS mode according to one embodiment.

FIG. 6 shows a flowchart of the SOS mode. In this mode, a countdown timer is initiated, requiring the user to type a preset personal identification number (PIN) number before expiration of a countdown timer. If the preset PIN number is not entered before the countdown timer expires, then a sequence of notifications may be triggered. In this manner, a user is able to have a help message sent to a third party assistance provider 108 (see FIG. 1), such as the police, in the event they are in danger and unable to directly contact the third party assistance provider 108 themselves. This mode may be implemented by the user device 102 or in combination with the tethered device 104, and the mode may be performed within various system environments, such as those shown in FIGS. 1-1C. The below description of the SOS mode is made in reference to the system environment shown in FIG. 1 whereby the user device 102 is provided with a touch-screen graphic interface display. However, in other embodiments, use of a touch-screen graphic display is not required as other suitable input devices of the user device 102 may be utilized.

Prior to using the SOS mode, a password, such as a PIN number, that can deactivate a countdown timer by entering the password at the user device 102 (see FIG. 1) must be set. Non-limiting examples of the password can be a combination of text, numbers, and symbols, swipe patterns or a dictated message that can be received by a microphone of the user device 102.

After setting a password, the SOS mode may be executed by the user device 102. Step 602 shows a start screen displayed on the touch-screen graphic interface of the user device 102. The start screen displays the various modes that a user can select from, including the SOS mode. In this example, the user has already set a PIN number as a password. In an embodiment, the user can select and initiate the SOS mode using the touch-screen interface. Typically, the user will initiate the SOS mode in a moment of danger such as a carjacking or kidnapping.

At step 604, the SOS mode has commenced, and a countdown timer 604 has started. A graphic interface displayed on the user device 102 generally displays a continuously decreasing time value corresponding to the countdown timer 604 and a touch-sensitive cancel button that allows the user to access a graphic interface display whereby the user can enter a PIN number using the touch-sensitive display on the graphic interface. In an embodiment, the graphic interface may display the decreasing time value in increments of 1 second, 5 seconds, or any other time value. In an embodiment, the time value increment can vary depending on the time remaining in the countdown timer 604.

In an embodiment, the countdown timer 604 relates to the maximum amount of time that the preset password must be entered before a triggering event occurs, which in this case is the expiration of the countdown timer 604. The countdown timer 604 can be any time value, such as 15 seconds or 60 seconds. In an embodiment, the time value of the countdown timer 604 can depend on device collected or user provided information. For example, the time value of the countdown timer 604 may automatically decrease when the user is farther away from a preset location or during nighttime hours. In an embodiment, the time value may be preconfigured by the user or by the server 106.

At step 612, the timer 604 has expired prior to successful entry of the password. The expiration of the timer 604 functions as a triggering event that sends device collected information, such as a location of the user device 102, to the server 106 (see FIG. 1), which in turn sends a notification message including the location and a distress message to preset contact(s), and/or the monitoring provider 112 and the third party assistance provider 108. In certain embodiments, upon expiration of the timer 604 the user device 102 will send the location as device collected information more than once. In this embodiment, the location of the user device 102 is sent to the server 106 periodically such that the movement of the user device 102 can be tracked by the monitoring provider 112 and/or the third party assistance provider 108.

At step 606, the user has selected the cancel timer option prior to the expiration of the timer 604. Selecting the cancel timer option brings up the password entering interface that prompts the user to enter the preset PIN number, using the touch-sensitive display on the graphic interface. In some embodiments, the graphic interface display may provide ten touch-sensitive buttons with each button corresponding to a number from zero through nine. In some embodiments, the graphic interface display may provide fewer than ten touch-sensitive buttons. For example, in an embodiment the touch-screen graphic interface display only provides a subset of buttons in order to conserve screen space on the touch sensitive display. For instance, if the password is a four digit PIN number, the password entering interface may only include the four digits of the PIN displayed in a random order such that guessing the order of numbers is not likely to be achieved prior to expiration of the timer 604.

At step 610, the user has entered an incorrect PIN. The graphic interface display indicates unsuccessful entry of the PIN by returning to the home screen of the SOS mode, which places the user back to the timer 604 that is still counting down. If the user desires to attempt to enter the password again, then the cancel option must be selected a second time. In an embodiment, the number of attempts to enter the correct password is limited to the duration of the timer 604 before the alert is sent 612.

Going Out Mode

Figure 7:
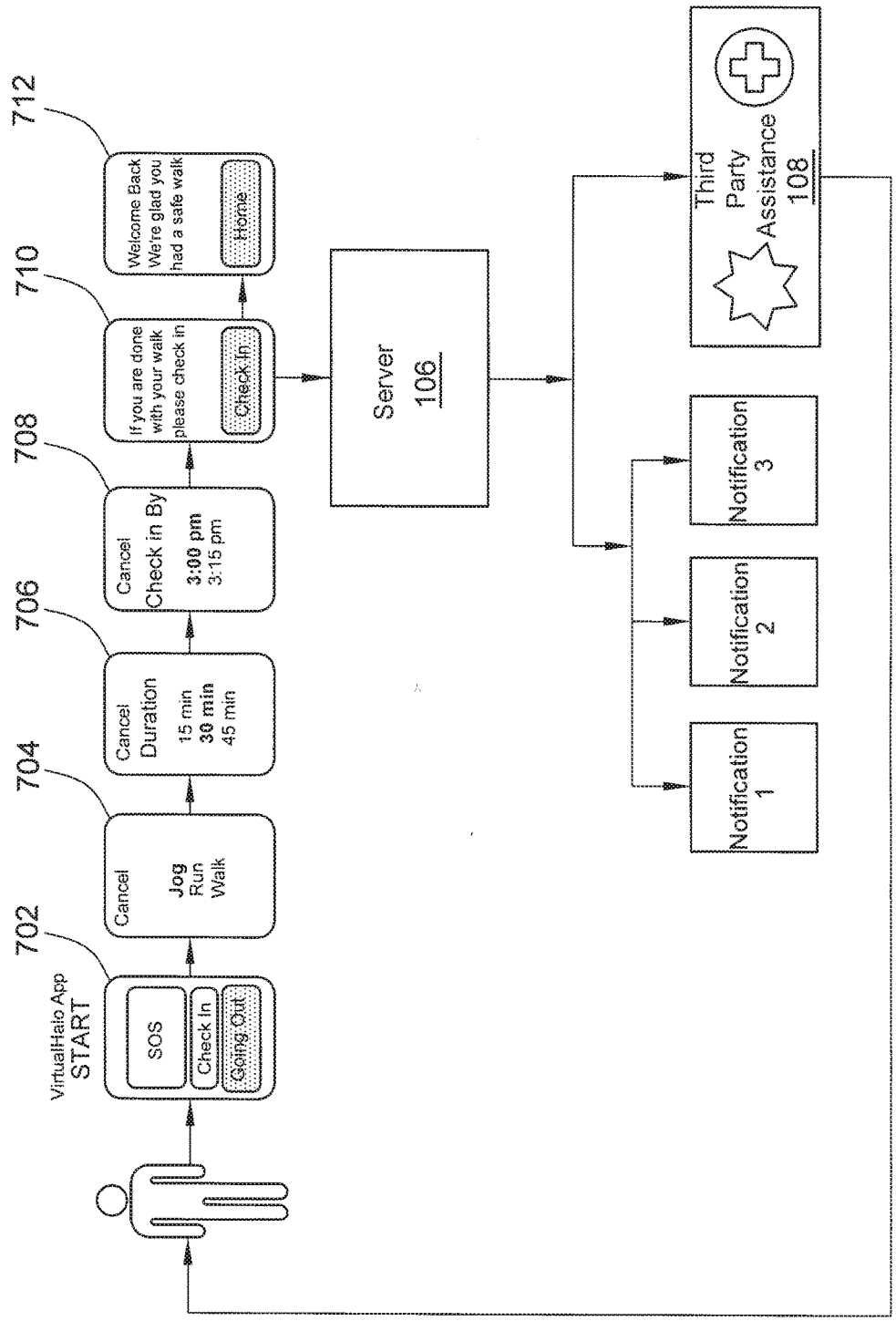
FIG. 7 is a flowchart illustrating the Going-Out mode according to one embodiment.

FIG. 7 shows a flowchart of the Going Out mode. In this mode, a user can select an activity and associated time duration, and notification messages may be triggered if the user has not indicated completion of the activity within the time duration. This example mode may be implemented by the user device 102 or in combination with the tethered device 104, and the mode may be performed within various system environments, such as those shown in FIGS. 1-1C. The below example of the Going Out mode is made in reference to the system environment shown in FIG. 1 whereby the user device 102 is provided with a touch-screen graphic interface display. However, in other embodiments, use of a touch-screen graphic display is not required as other suitable input devices of the user device 102 may be utilized.

Step 702 shows a start screen displayed on the touch-screen graphic interface. The start screen displays the various modes that a user can select from, including the Going Out mode. Upon selection of the Going Out mode, the application proceeds to step 704. At step 704, the graphic interface of the user device 102 prompts the user to choose from a predetermined list of various activities or input a custom activity. The list of various activities generally pertains to activities in which a user may temporarily leave her current destination, such as various sports or outdoor related activities. Some non-limiting examples include biking, a date, going to a friends house, jogging, walking, and hiking. In an embodiment, the graphic interface enables the user to input an activity using the touch screen graphic interface input device 214 (see FIG. 2).

At step 706, the application of the user device 102 (see FIG. 1) prompts the user to enter a time duration. In an embodiment, the time duration relates to the duration in which the user expects to complete the activity selected in step 704. The time duration may be expressed as a specific time of the day, such as 3:05 PM, or may be expressed as an absolute value of minutes and hours. In an embodiment, the user is permitted to input other information relating to the selected activity, such as location information of where the selected activity may take place.

At step 708, the application causes the user device 102 (see FIG. 1) to prompt the user to enter a check-in time. The check-in time may be expressed as a specific time of the day or as an absolute value of minutes and hours. In an embodiment, the check-in time corresponds to an upper time limit in which the user must complete a check-in step.

The server 106 proceeds to monitor for the expiration of the time duration set in step 706 or for whether the preset check in time is reached as set at step 708. Upon expiration of the time duration or coming to the preset time, at step 710, the application causes the user device 102 (see FIG. 1) to prompt the user to check in by selecting a check in option displayed on the user device 102. FIG. 7A illustrates this prompt, in accordance with one embodiment. And upon the user checking in, at step 712, the user device 102 shows a graphic interface displayed by the user device 102 that directs the user back to a home page of the application.

In an embodiment of the Going Out mode, a triggering event occurs if the user does not successfully complete the check-in step before the time value corresponding to step 708. In an embodiment, the triggering event varies based on user provided information, device collected information, or any combination thereof. In an example embodiment, the server 106 (see FIG. 1) does not receive the check-in step from the user device 102 indicating the Going Out mode has been completed within the time indicated at step 708, triggering an alert. The alert may include user provided information, such as the selected activity from step 704, the duration from step 706 and the check-in time from step 708. The alert may also include device collected information, such as location information or other information collected through any of the various input devices described above.

In an embodiment, the server 106 (see FIG. 1) then triggers any of various notifications to any of various destinations, such as the monitoring provider 112 or the third party assistance provider 108. The content, type, and destinations may vary based on user provided information and device collected information. As an example of user provided information, the user may preset notification message content and one or more recipients of any notification messages. As an example of device collected information, the type of notification message may include location information. For example, the user may configure, within the user device 102, to initiate only one notification message, whereby the notification is sent to the user's neighbor (functioning as the monitoring provider 112) if the user has not completed the check-in step after a brief walk, and if the location information indicates the user was recently within a certain proximity to the neighbor. Based on the location information sent to the server 106, other user contacts functioning as the monitoring provider 112 may be contacted as well. The number, content, and type of notifications and the recipients of the notifications are not intended to be limited to any particular configuration.

In certain embodiments, algorithms and/or artificial intelligence executed by the service provided by the server 106 (see FIG. 1) or the application executed by the user device 102 can tell if the user is in distress and take appropriate action. For instance, if a remote sports related emergency occurs, such as a hiker in trouble in Yosemite, or a sailboat in distress, the user device 102 can ping a distress signal through all available wireless methods, to the server 106 to summon assistance. This can be activated either actively by input from the user or passively, where the application executed by the user device 102 or through the above mentioned algorithm and/or artificial intelligence.

An additional "where am I" feature may be implemented in this mode. This feature allows the user to query the user device 102 to provide the closest address, mile marker, coordinates or any other pertinent information providing an indication of the user's location.

Check-In Mode

Figure 8:
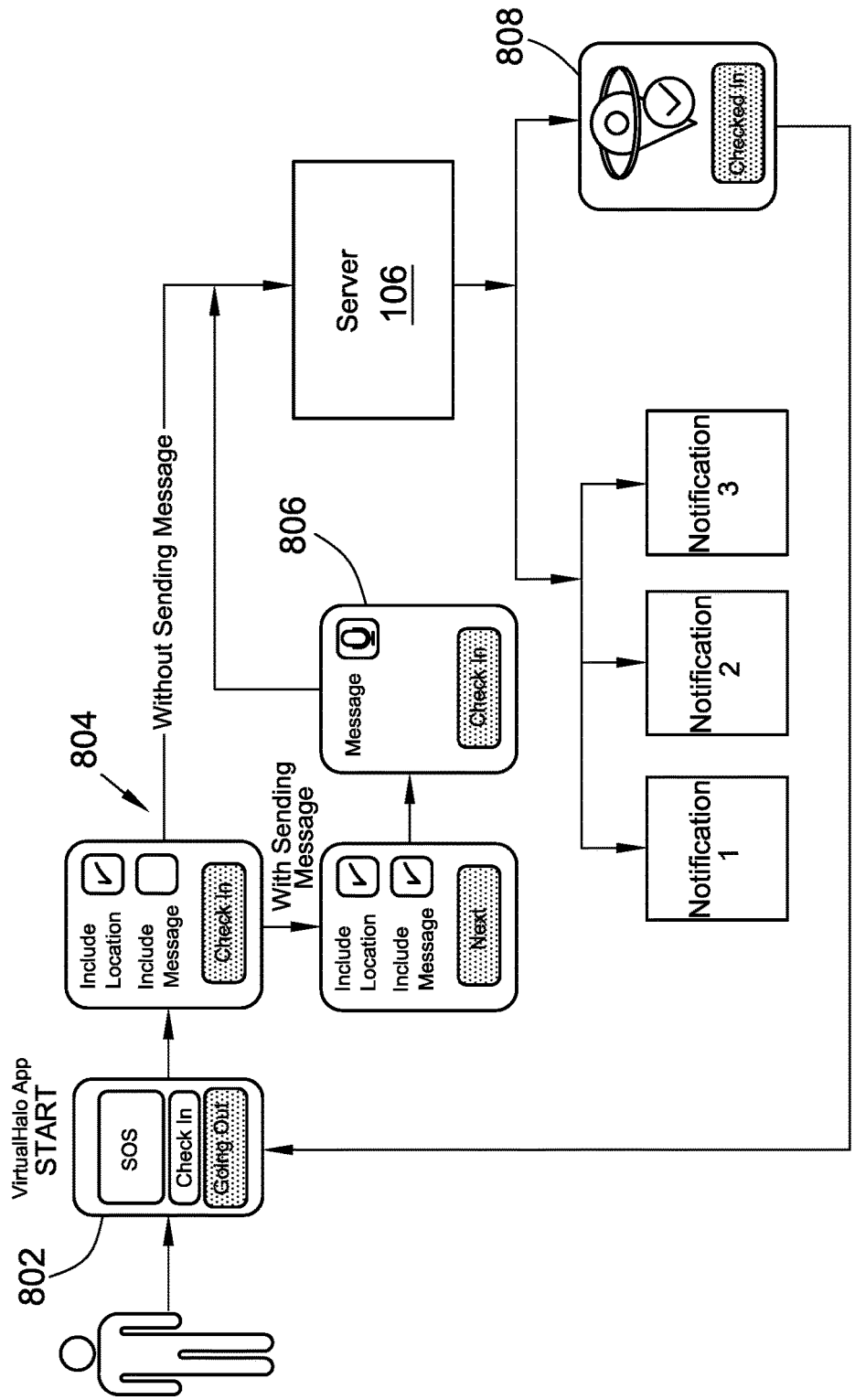
FIG. 8 is a flowchart illustrating the Check-In mode according to one embodiment.

FIG. 8 shows a flowchart of the Check-in mode. This mode allows a user to conveniently send notification messages to at least one preset destination, whereby the notification may include a location and/or a configurable message. This example mode may be implemented by the user device 102 or in combination with the tethered device 104, and the mode may be performed within various system environments, such as those shown in FIGS. 1-1C. The below example of the Check-in mode is made in reference to the system environment shown in FIG. 1 whereby the user device 102 is provided with a touch-screen graphic interface display. However, in other embodiments, use of a touch-screen graphic display is not required as other suitable input devices of the user device 102 may be utilized.

Figure 8A:
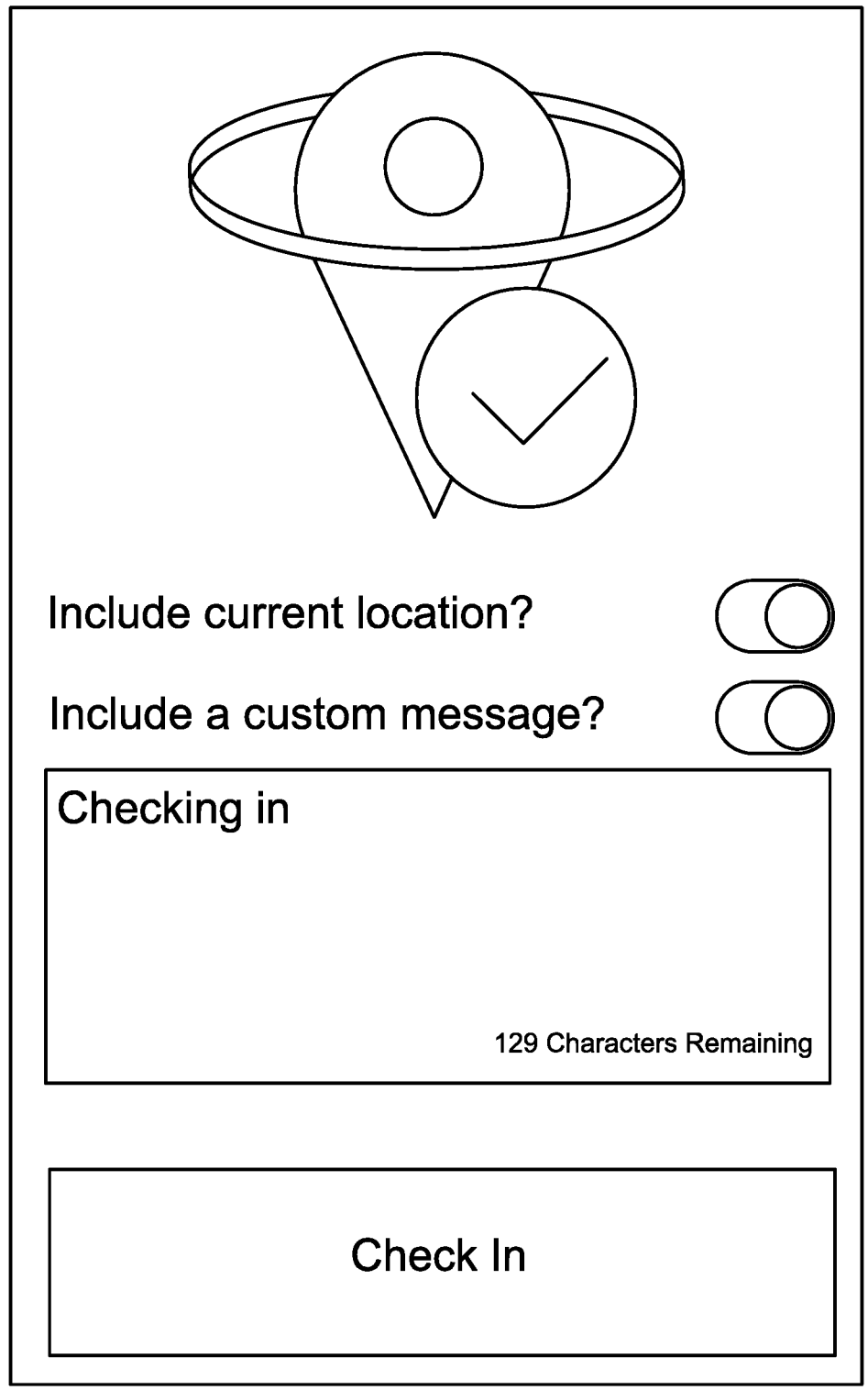
FIG. 8A illustrates an example graphic interface display associated with the Check-In mode according to one embodiment.

Step 802 shows a start screen displayed on a touch-screen graphic interface of the user device 102 (see FIG. 1), according to an example embodiment. The start screen displays the various modes that a user can select from, including the Check-in mode. After the user selects the Check-in mode option, at step 804, the graphic interface displays a check-in screen. In the illustrated embodiment shown in FIG. 8, the check-in screen includes text, at least one touch-sensitive button configured to allow the user to proceed with the check-in process, and at least one check-box. The text, touch-sensitive buttons, and check-box can vary based on user provided and device collected information. In an embodiment, at least one check-box allows the user to input user provided information and device collected information. For example, as shown at step 804, a check-box may allow the user to include location information (representing device collected information), and another check-box may allow the user to include a message, such as text, audio, video, or any combination thereof (user provided information). In an embodiment, when the include a message check-box is selected, the touch sensitive button changes from a Check-In button to a Next button, as shown at step 805. When the user selects the Next button, the message may be input in a subsequent graphic interface display, as shown at step 806. In the illustrated embodiment, step 806 shows a touch-sensitive Check-In button that when selected by the user will cause the Check-In message to be sent. In other embodiments, the check-box and touch-sensitive button can be replaced with another suitable method of providing input. For example, the check-box can be replaced with a toggle switch, such as shown in FIG. 8A.

After the user selects the Check-In button, the user device 102 (see FIG. 1) sends a message including the device collected information and/or the user provided information to the server 106. The server 106 is then alerted that the user has completed steps 804 or 806 when it receives the Check-In message, which functions as a triggering event for the server 106. The server 106 then sends one or more notification messages to any of various destinations. The content, type, and destinations may vary based on user provided information and device collected information. As an example of user provided information, the user may preset notification content and recipients such as the monitoring provider 112. The notification may also include information obtained in steps 804 and 806. The number, content, and type of notifications and the recipients of the notifications are not intended to be limited to any particular configuration.

I'm OK Mode

Figure 9A:
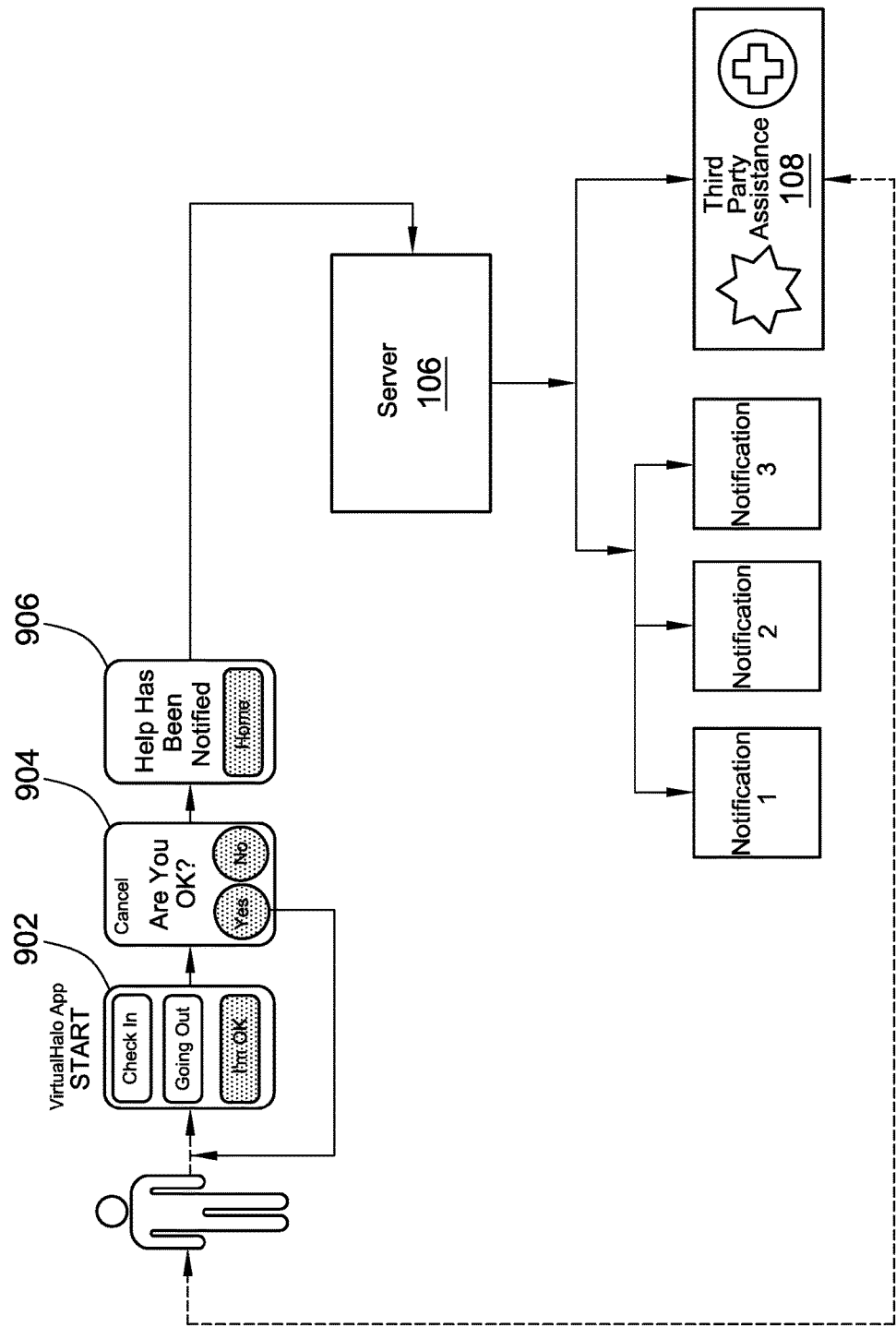
FIG. 9A is a flowchart illustrating the I'm OK mode according to one embodiment.
Figure 9B:
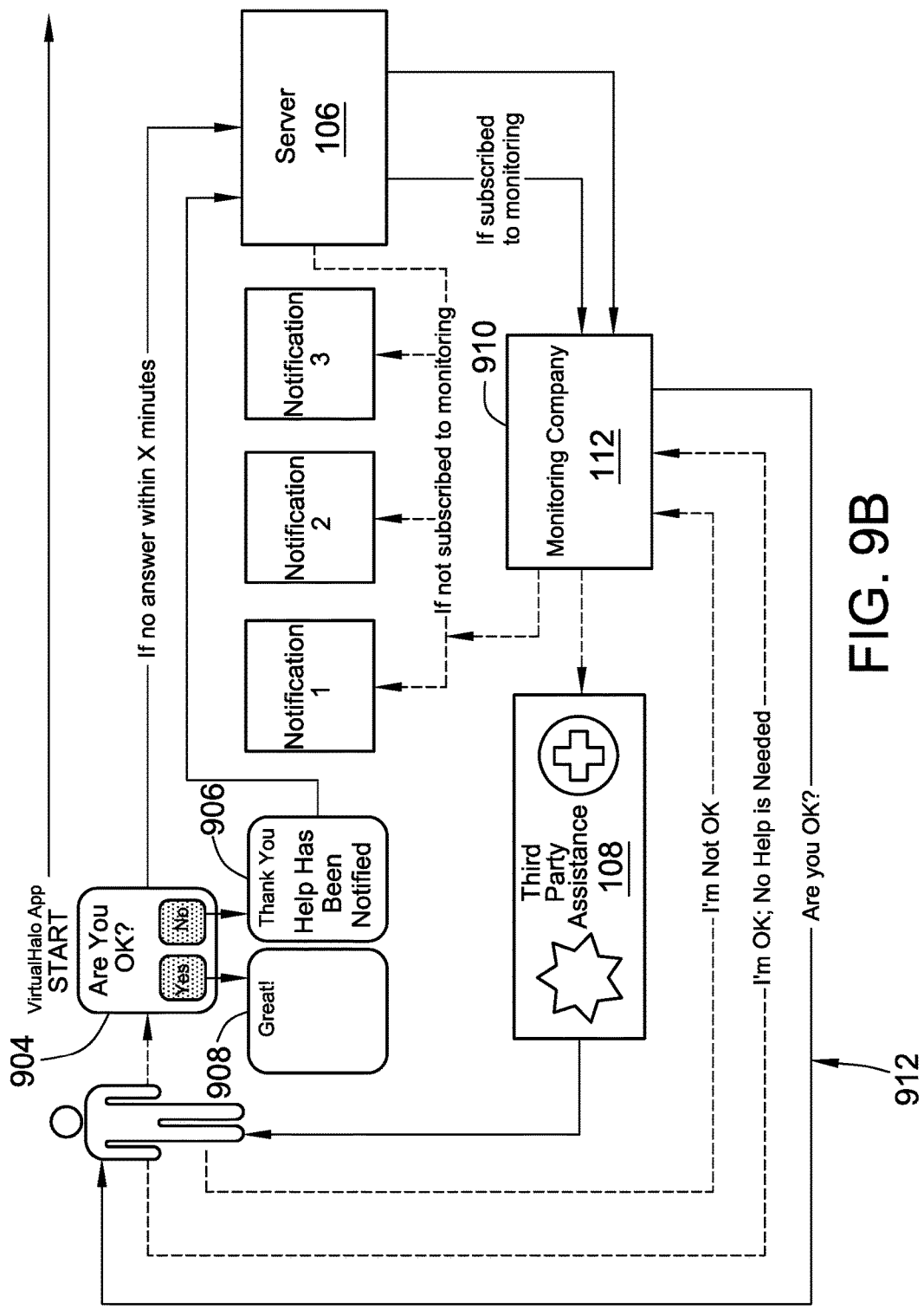
FIG. 9B is a flowchart illustrating the I'm OK mode according to another embodiment.

FIGS. 9A and 9B show flowcharts of two example embodiments of the I'm OK mode. In this mode, a series of notifications may be triggered based on user input into the user device 102 (see FIG. 1) indicating that assistance is needed. This example mode may be implemented by the user device 102 or in combination with the tethered device 104, and the mode may be performed within various system environments, such as those shown in FIGS. 1-1C. The below examples of the I'm OK mode is made in reference to the system environment shown in FIG. 1 whereby the user device 102 is provided with a touch-screen graphic interface display. However, in other embodiments, use of a touch-screen graphic display is not required as other suitable input devices of the user device 102 may be utilized.

Referring to the example shown in FIG. 9A, step 902 shows a start screen displayed on the touch-screen graphic interface. The start screen displays the various modes that a user can select from, including the I'm OK mode. In this example, the user has already been authenticated, in any suitable manner as described above. In an embodiment, the user can select and initiate the I'm OK mode using the touch-screen interface.

At step 904, the graphic interface of the user device 102 (see FIG. 1) displays text and at least one touch-sensitive button. In an embodiment as shown in FIG. 9A, the user is prompted to indicate whether assistance may be needed with text, such as "Are you OK." In the embodiment shown in FIG. 9A, one touch-sensitive button represents a "Yes" response and the other represents a "No" response. In an embodiment, the displayed text and the touch sensitive buttons may vary based on user provided information and device collected information. In an embodiment shown in FIG. 9A, if the "Yes" response is chosen, the graphic display interface returns to the start screen 902. In other embodiments where communication between the user device 102 and the server 106 is bidirectional, the graphic interface may display text confirming the user's response (see FIG. 9B).

At step 906, the user has indicated that assistance is needed. The user indicating that she is not OK by responding No to the question "Are You OK," in the illustrated embodiment, functions as a triggering event by having an alert is sent to the server 106 by the user device 102 (see FIG. 1) that indicates that the user is not OK. In an embodiment, the alert varies based on user provided information, device collected information, or any combination thereof. The server 106 receives the alert and configures a notification message to send to a previously configured recipient, such as the monitoring provider 112. The notification message indicates that the user needs assistance, and the alert may also include user provided information such as health information like sex, height, weight, allergies, prescribed medications, blood type, etc. The alert may also include device collected information, such as location information or other information collected through any of the various input devices described above.

The content, type, and destinations of the notification messages sent by the server 106 (see FIG. 1) may vary based on user provided information and device collected information. As an example of user provided information, the user may preset notification content and recipients, such as the monitoring provider 112. As an example of device collected information, the server 106 may notify the third party assistance provider 108 or paramedics if the user is located beyond a preconfigured distance from her home, if blood pressure is above a threshold or blood sugar level below a threshold. If, for example, any of these parameters are not met, the server 106 may notify a friend or family member of the user. The number, content, and type of notifications and the recipients of the notifications are not intended to be limited to any particular configuration.

FIG. 9B illustrates an example of how the I'm OK mode can be configured. Returning to step 904, the graphic interface displays text prompting the user to indicate whether she is OK. In the illustrated embodiment, the application executed by the user device 102 is prompted to run the I'm OK mode by a setting in the user device 102 and/or by the server 106. Similar to FIG. 9A, the user device 102 is configured to react according to the user's indication of whether she is OK or not OK. However, as shown in FIG. 9B, the I'm OK mode of the application executed by the user device 102 can be configured such that a triggering event occurs if the user does not respond within a preset time period. The preset time period can vary based on user provided and device collected information or is a preset value provided by the user during configuration of the I'm OK mode. Upon expiration of the time period, an alert is sent to the server 106. The alert can be similar to the alert at step 906 described above, and may indicate the user's nonresponse.

The server 106 may respond as described above with respect to FIG. 9A or in various other manners. As shown in FIG. 9B, after the occurrence of the triggering event, which in the illustrated embodiment is the expiration of the time period without a response from the user, the server 106 may notify the monitoring provider 112. In an embodiment, the server 106 notifies the monitoring provider 112 based on device collected and/or user provided information. In an embodiment, the notification to the monitoring provider 112 may include various user provided and device collected information.

At step 910, the monitoring provider 112 may then react in various manners. In an embodiment, the monitoring provider 112 may react based on user provided and device collected information. For example, at step 912, the monitoring provider 112 may contact the user, such as through voice communication between the user device 102 or tethered device 104. Alternatively or additionally, the monitoring provider 112 may notify a friend or family member of the user that has previously been provided to the monitoring provider 112. In an example embodiment, the monitoring provider 112 may notify third party assistance 108 or paramedics, if the monitoring provider 112 is unable to establish voice communication with the user device 102 or tethered device 104. The number, content, and type of notifications and the recipients of the notifications are not intended to be limited to any particular configuration. Alternatively, the server 106 may also directly send the notification messages, including the device collected information and the user provided information, to preconfigured recipients.

GoldenHalo Mode

Figure 10:
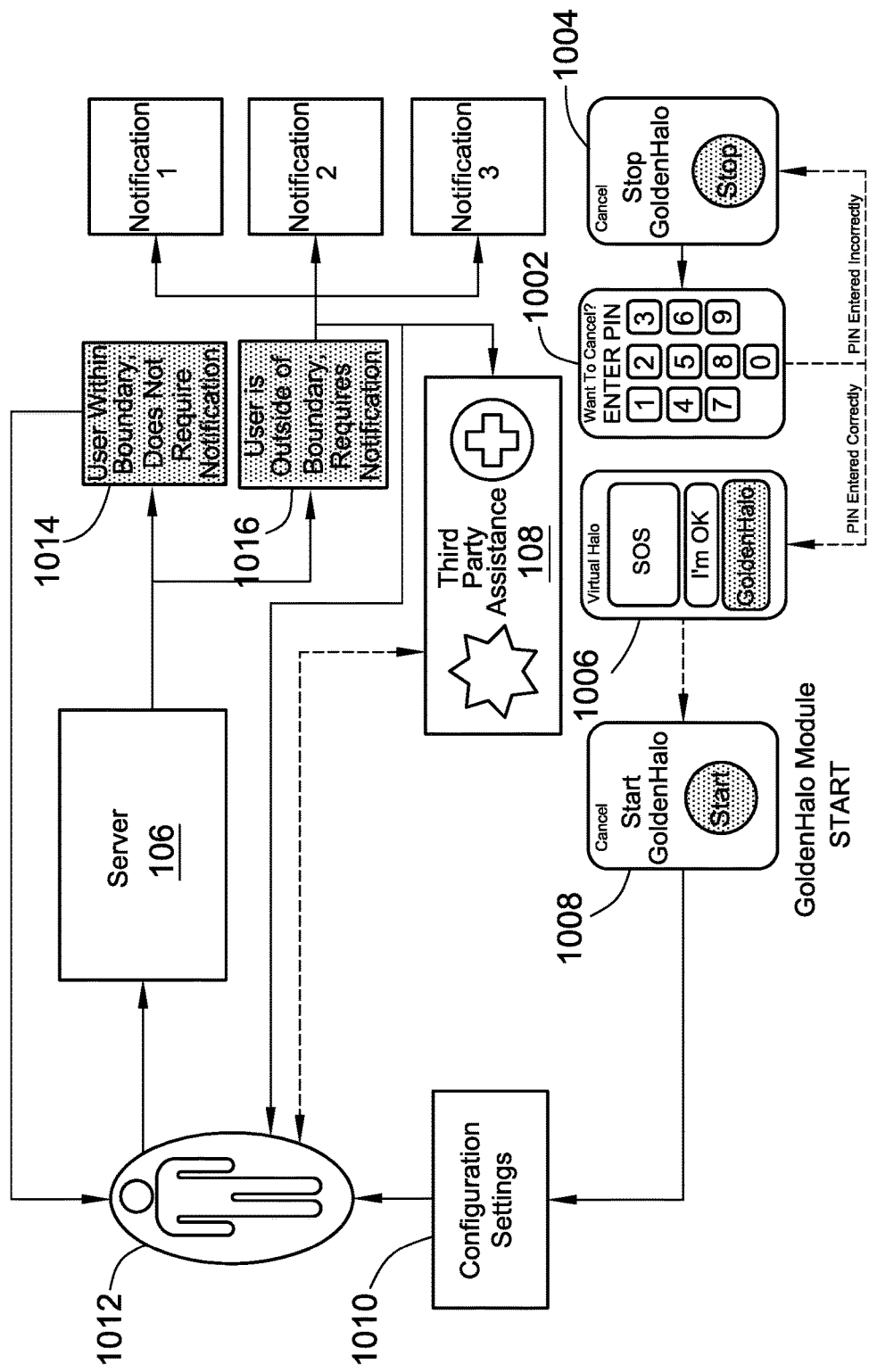
FIG. 10 is a flowchart illustrating the GoldenHalo mode according to one embodiment.

FIG. 10 shows a flowchart of the GoldenHalo mode. In this mode, a series of notification messages may be triggered depending on a user's location and other device collected information. This example mode may be implemented by the user device 102 or in combination with the tethered device 104, and the mode may be performed within various system environments, such as those shown in FIGS. 1-1C. The below example of the GoldenHalo mode is made in reference to the system environment shown in FIG. 1 whereby the user device 102 is provided with a touch-screen graphic interface display. However, in other embodiments, use of a touch-screen graphic display is not required as other suitable input devices of the user device 102 may be utilized.

At step 1006, the graphic interface displays the various modes that a user can select from, including the GoldenHalo mode. At step 1008, a graphic interface illustrating the GoldenHalo start screen is shown. In an embodiment, a touch-sensitive button on the graphic interface permits the user to initiate the mode. At step 1010, the graphic interface display permits the user to adjust configuration settings. In an embodiment, a user can adjust configuration settings using a touch-screen graphic interface on the user device 102. In general, configuration of settings is optional after an initial setup procedure. In an embodiment, configuration of settings can be accomplished using the tethered device 104 or a web interface accessible through an internet connected device. Typically, configuration of settings has been performed prior to step 1010 during an initiation of the GoldenHalo mode.

The configuration settings generally relate to user provided information and device collected information, and may also allow the user to adjust any other setting to further the objective of the GoldenHalo mode. For example, a user can indicate a geographic region that the user device 102 is to remain within, such that a triggering event occurs if the user device 102 exits that geographic region. An example geographic region may be a circular region, within a one mile radius, and centered on a particular reference point. Other non-limiting examples of user provided information include the user's age, weight, health conditions, allergies, prescribed medications, and blood type. Device collected information can include geographic movements, motion activity, heart rate, blood pressure, blood sugar level, and any other information that can be obtained through an input device. In an embodiment, the user can also configure various thresholds, such as the maximum time the user device 102 can remain outside a preconfigured geographic region. In an embodiment, the user provided information and device collected information is transmitted to the server 106 and stored at the server 106.

At step 1012, the GoldenHalo mode operates in accordance with the configuration settings. The GoldenHalo mode generally monitors device collected information, and in particular location information, but is not limited to any particular type of device collected information. The GoldenHalo mode is generally configured such that device collected information is received by the server 106 and analyzed to determine whether a triggering event has occurred. In an example embodiment, after a user sets a maximum time the user device 102 can remain outside a preconfigured geographic region, a triggering event may occur when the user device 102 is outside the preconfigured geographic region and the time limit threshold is exceeded. In the illustrated embodiment shown in FIG. 10, the server 106 receives the user provided and device collected information, and determines whether a triggering event has occurred, which in this case is the user device 102 leaving a preconfigured geographic region. In other embodiments, this may be accomplished by the user device 102, the tethered device 104, the user monitoring provider 112, or any combination thereof.

At step 1016, the server 106 (see FIG. 1) has determined a triggering event has occurred. The server 106 is generally configured to initiate at least one notification message. Notification messages may be sent to the user, the third party assistance provider 108, the monitoring provider 112, or any other recipient that the user has set up within the service executed at the server 106. Notification messages may vary depending on the triggering event and various combinations of user provided and device collected information. For example, if the user device 102 is located outside a geographic region for a first period of time, a notification may be sent to the user to return home. In an embodiment, if the user device 102 is located outside the geographic region for a second period of time, additional notifications may be sent to third party assistance provider 108 or other recipients. The content, type, and destination of notification may vary based on user provided information and device collected information, as discussed above.

At step 1014, the server 106 (see FIG. 1) has determined that a triggering event has not occurred based on the received device collected information, such as geographic location of the user device 102. As illustrated, the GoldenHalo mode continues operating as described in step 1012. In an embodiment, the GoldenHalo mode may terminate after a preset time or may terminate based on user provided and collected information.

At step 1002, a user desiring to disable the GoldenHalo mode must be authenticated by the user device 102. In certain embodiments, the authentication can be accomplished by entering a personal identification number (PIN) on a touch-sensitive graphic interface of the user device 102. Authentication may be performed by any number of methods, such as biometric or password. If authentication is unsuccessful, then the user device 102 will disable the GoldenHalo mode.

Latchkey Mode

Figure 11:
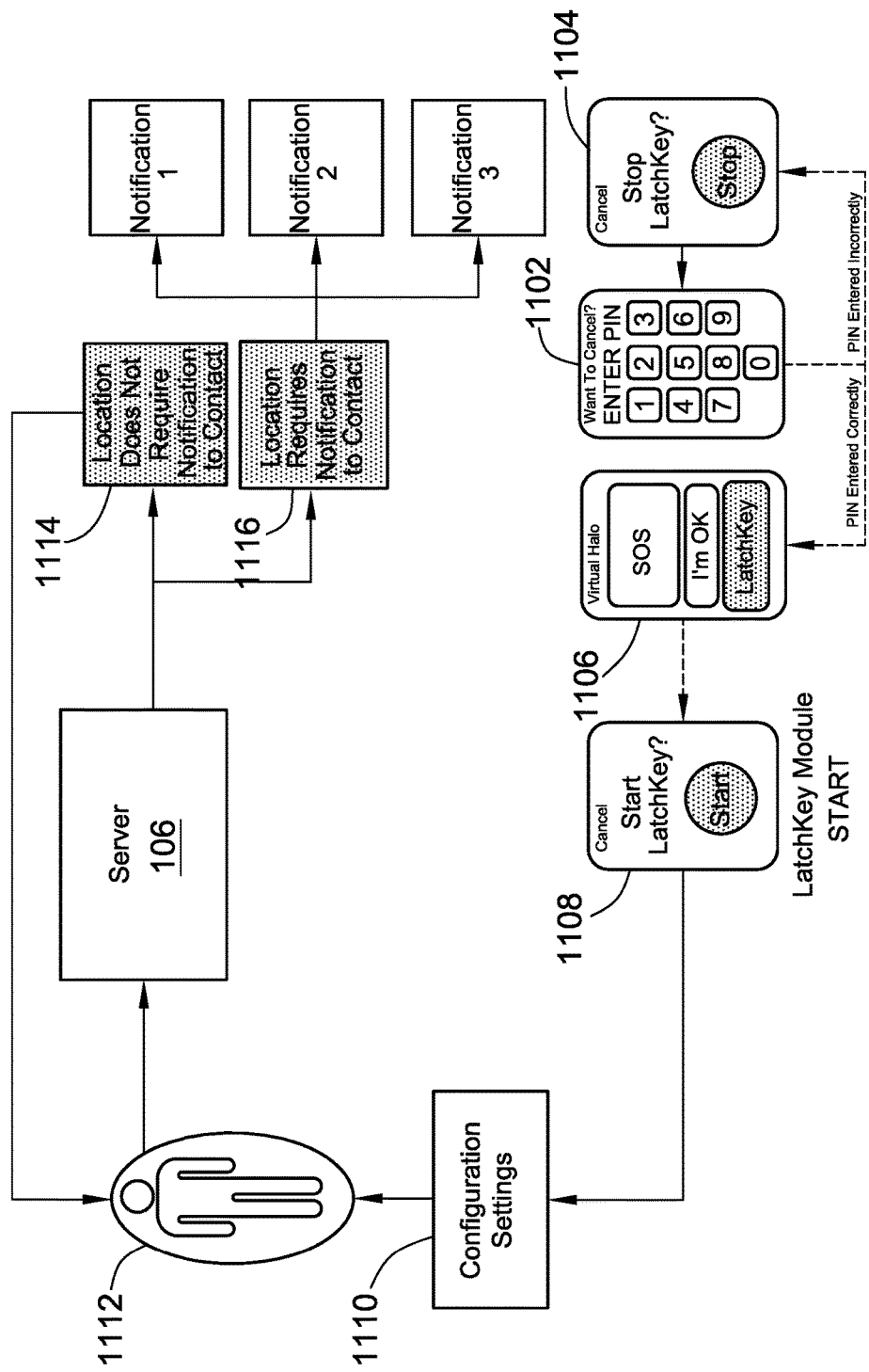
FIG. 11 is a flowchart illustrating the LatchKey mode according to one embodiment.

FIG. 11 shows a flowchart of the Latchkey mode. In this mode, a notification message may be triggered when the user enters or exits a preset geographic area. This mode is similar to the GoldenHalo mode but more focused on a user entering or exiting a preset geographic location. For instance, in one embodiment, the Latchkey mode may be used to send notification messages if the user device 102 leaves a previously defined geographic location, such as the user's home or school.

The Latchkey mode may be implemented by the user device 102 or in combination with the tethered device 104, and the mode may be performed within various system environments, such as those shown in FIGS. 1-1C. The below example of the Latchkey mode is made in reference to the system environment shown in FIG. 1 whereby the user device 102 is provided with a touch-screen graphic interface display. However, in other embodiments, use of a touch-screen graphic display is not required as other suitable input devices of the user device 102 may be utilized.

At step 1106, the graphic interface displays the various modes that a user can select from, including the LatchKey mode.

At step 1108, a graphic interface illustrating the LatchKey start screen is shown. In an embodiment, a touch-sensitive button on the graphic interface permits the user to initiate the mode.

At step 1110, the graphic interface display permits the user to adjust configuration settings. In other embodiments, configuration of settings has been performed prior to step 1110. The configuration settings generally relate to user provided information and device collected information, and may also allow the user to adjust any other setting to further the objective of the Latchkey mode. For example, a user can indicate specific geographic locations that the user device 102 is expected to arrive to or depart from. In an example embodiment, a user can set her home as a first geographic location and a child's school as a second geographic location. In an embodiment, a user can set the location information and configure other settings using a touch-screen graphic interface on the user device 102. In other embodiments, this may be accomplished using the tethered device 104 or a web interface accessible through an internet connected device with access to the user account within the server executed by the server 106.

Additionally, any other user provided and device collected information may be configured, similar to the configuration settings described in relation to FIG. 10. In an embodiment, the user can also configure various limits and thresholds, such as when the user device 102 is expected to enter or depart from a particular geographic location. In an embodiment, the user provided information and device collected information is transmitted to the server 106 and stored at the server 106.

At step 1112, the LatchKey mode operates in accordance with the configuration settings. The Latchkey mode generally monitors device collected information, and in particular location information, but is not limited to any particular type of device collected information. The LatchKey mode is generally configured such that device collected information is received and analyzed to determine whether a triggering event has occurred. In an embodiment, a triggering event may occur when location information relating to the user device 102 indicates the user device 102 has not arrived at a particular location before a particular time. For example, a parent may configure the user device 102, which in this embodiment is worn and/or carried by a child, to initiate an alert if the child does not arrive home after school within one hour after the child's final class. Triggering events are not limited to any particular combination of user provided and device collected information. In an embodiment shown in FIG. 11, the server 106 receives the user provided and device collected information, and determines whether a triggering event has occurred. In other embodiments, this may be accomplished by the user device 102, the tethered device 104, the user monitoring provider 112, or any combination thereof.

At step 1116, the server 106 has determined a triggering event has occurred. The server 106 is generally configured to initiate at least one notification message. Notification messages may be configured to be sent to any recipient. Notifications may vary depending on the triggering event and various combinations of user provided and device collected information. For example, a first notification may be sent to the user device 102 after a first period of time, and additional notifications may be sent to other recipients after a second period of time. The content, type, and destination of notification may vary based on user provided information and device collected information.

At step 1114, the server 106 has determined that a triggering event has not occurred based on the received user provided and device collected information. In absence of a triggering event, the Latchkey mode continues operating as described in step 1112. In an embodiment, the Latchkey mode may terminate after a preset time or may terminate based on user provided input in step 1104.

At step 1102, a user desiring to disable the LatchKey mode must be authenticated by the user device 102. In certain embodiments, the authentication can be accomplished by entering a personal identification number (PIN) on a touch-sensitive graphic interface of the user device 102. Authentication may be performed by any number of methods, such as biometric or password. If authentication is unsuccessful, then the user device 102 will disable the LatchKey mode.

Breadcrumb Mode

Figure 12:
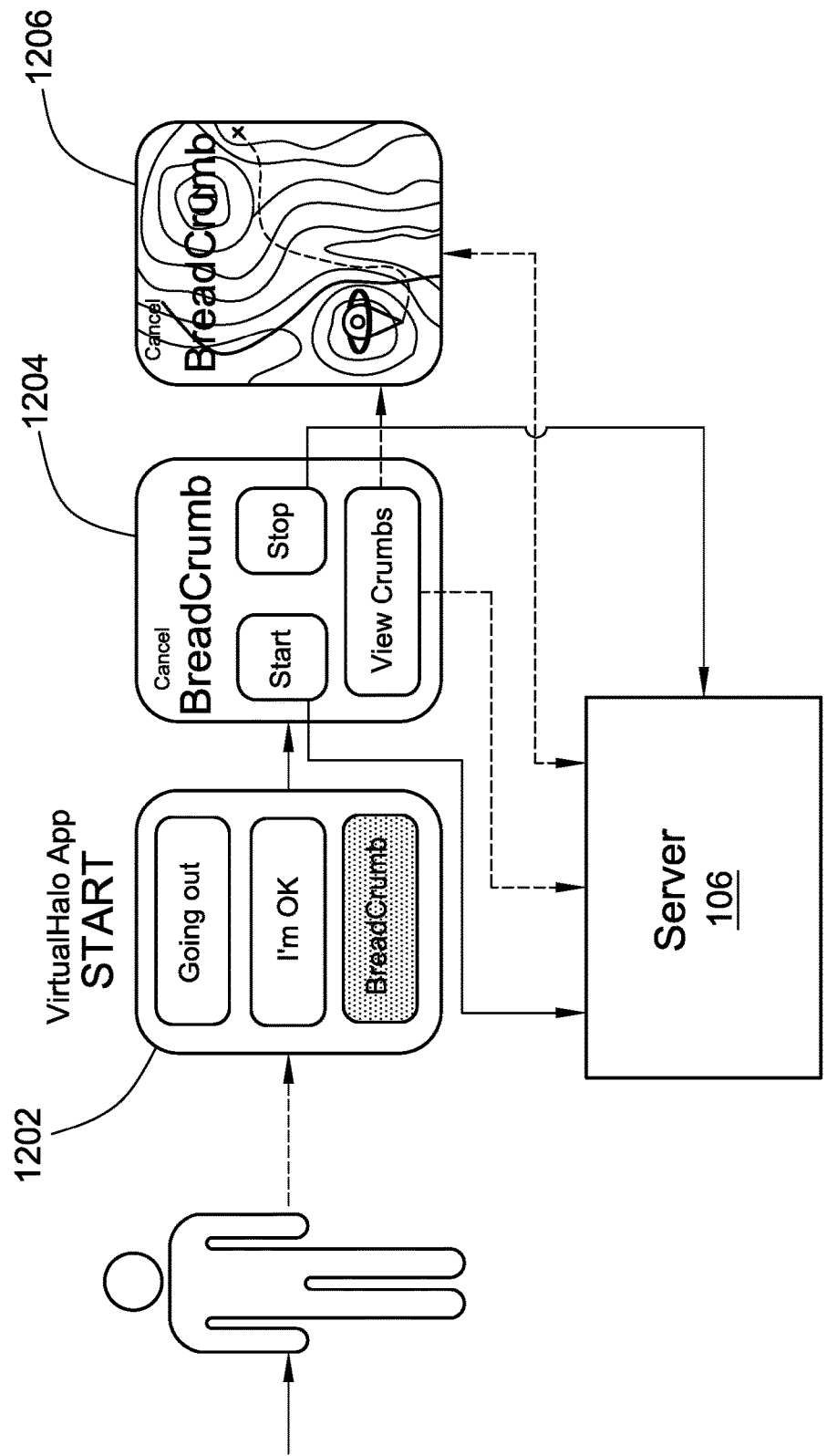
FIG. 12 is a flowchart illustrating the BreadCrumb mode according to one embodiment.

FIG. 12 shows a flowchart of the Breadcrumb mode. In this mode, the user device 102 captures its geographical location and may store it in the device 102 and transmits it along with a timestamp to the server 106, where the location and time information may then be accessed by the user or a third party with access to the user's private account information stored at the server 106.

The Breadcrumb mode may be implemented by the user device 102 or in combination with the tethered device 104, and the mode may be performed within various system environments, such as those shown in FIGS. 1-1C. The below example of the Breadcrumb mode is made in reference to the system environment shown in FIG. 1 whereby the user device 102 is provided with a touch-screen graphic interface display. However, in other embodiments, use of a touch-screen graphic display is not required as other suitable input devices of the user device 102 may be utilized.

Step 1202 shows a start screen displayed on the touch-screen graphic interface. The start screen displays the various modes that a user can select from, including the Breadcrumb mode. From the start screen, the user can select the Breadcrumb mode using the touch-screen interface such that the user device 102 initiates the Breadcrumb mode.

At step 1204, the graphic interface generally displays one or more touch-sensitive buttons that function to control operation of the Breadcrumb mode at the user device 102. In the illustrated embodiment shown in FIG. 12, the graphic interface displays three touch-sensitive buttons, including a start button. Upon selecting the start button on the touch-sensitive graphic display, the user device 102 then initiates a sequence in which the user device 102 periodically acquires the location of the user device 102, such as with the use of GPS, triangulation, or any other suitable means. The frequency that the user device 102 acquires location can vary based on user provided and device collected information. As an example of user provided information, the user may configure the user device 102 settings such that location is ascertained at intervals of 5 minutes, 10 minutes, or 30 minutes. As an example of device collected information, the user device 102 may ascertain location less frequently when the battery of the user device 102 decreases or if the location has not changed for longer periods of time, such as when a user is sleeping.

The user device 102 is generally configured to transmit to the server 106 each ascertained location information. In an embodiment, the server 106 is configured to store and log each instance of receiving location information. In an embodiment, the server 106 also stores a timestamp with each location transmission. As shown at step 1206, using the stored location information and the related timestamps stored at the server 106, a user may log into their account at the service executed by the server 106 to access this information in order to track the location of the user device 102 over time. Several benefits can be gained using the Breadcrumb mode, such as allowing a user to track and find a lost or stolen user device 102 or missing person.

In certain embodiments, the server 106 may be configured to send notification messages based on triggering events, which may be based on user provided and device collected information. For example, the server 106 may notify the third party assistance provider 108 and the user monitoring provider 112 if the location information indicates the user device 102 is within a particular remote location for an extended period of time. In this instance, the period of time the user device 102 is at a particular remote location acts as the triggering event. In this regard, the user is able to preset the period of time and certain known locations such that when the device is not located at one of the known locations, the server 106 is able to ascertain that the location is remote. The number, content, and type of notifications and the recipients of the notifications are not intended to be limited to any particular configuration.

In certain embodiments, the user device 102 may be configured to capture images, video and/or audio from an environment of the user device 102 upon the occurrence of a triggering event such as discussed above. In these embodiments, the user device 102 may collect images and/or video from an image sensor of the user device 102 and communicate those images to the server 106. Additionally, the user device 102 may capture audio from a microphone of the user device 102 and communicate that audio to the server 106. The user is then provided access to the images and audio by accessing her private account at the service executed by the server 106.

The graphic interface may also include other touch-sensitive buttons. In the example embodiment shown in FIG. 12, the graphic interface also includes a stop button, which then terminates the sequence of acquiring location information. The example embodiment in FIG. 12 shows a third button, called "View Crumbs" on the graphic interface, which allows the user to view the log of location information over a map interface or as discrete location and timestamp data points. In other embodiments, the displayed text and the touch sensitive buttons may vary based on user provided information and device collected information.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A portable electronic device, the portable electronic device comprising: a processor; a network interface for communicating with a wireless network; an input device for accepting user provided information from a user of the portable electronic device; one or more sensors for acquiring device collected information of the user of the portable electronic device; a memory comprising instructions for causing the processor to perform the steps of: collecting at least one of the user provided information and the portable electronic device collected information; and transmitting at least one of the user provided information and the portable electronic device collected information to a server for communicating a status to a user contact upon occurrence of a triggering event, wherein content of the status is based on at least one of the user provided information and the device collected information, and wherein the portable electronic device is configurable to operate in two or more of plurality of operation modes, the operation modes include: a health monitoring mode, an emergency countdown mode, an activity duration monitoring mode, a location, monitoring mode, an emergency contact mode, a geofence mode, a preset notification message mode, and a location tracking mode.

2. The portable device of claim 1, wherein the status is a notification message generated based on the at least one of the user provided information and the device collected information.

3. The portable device of claim 1, wherein the portable device is a wearable device tethered to a cellular phone.

4. The portable device of claim 1, wherein he portable device is a wearable device not tethered to a cellular phone.

5. The portable device of claim 1, wherein the status is provided to the user contact via one or more of: a pre-recorded robo-call message, a live phone call, an email, a text message, an application notification message, an operating system notification message, and a distress signal.

6. The portable device of claim 1, wherein the one or more sensors comprises an image sensor, and upon the occurrence of the triggering event, the image sensor captures one or more images.

7. The portable device of claim 6, wherein the memory further comprises instructions for causing the processor to perform the further steps of communicating the one or more images to the user contact.

8. The portable device of claim 1, wherein the one or more sensors comprises a microphone, and upon the occurrence of the triggering event, the microphone captures an audio signal in an environment around the portable device.

9. The portable device of claim 8, wherein the memory further comprises instructions for causing the processor to perform the further steps of communicating the audio signal to the user contact.

10. The portable device of claim 1, wherein the memory further comprises instructions for causing the processor to perform the further steps of causing a device tethered to the portable device to communicate one or more images captured by an image sensor of the tethered device or communicate an audio signal captured by a microphone of the tethered device.

11. The portable device of claim 1, wherein the memory further comprises instructions for causing the processor to perform the further step of indicating that the status of the user has been communicated to the user contact.

12. The portable device of claim 1, wherein the step of communicating the status occurs automatically without intervention from the user.

13. The portable device of claim 1, further comprising a Global Positioning System (GPS) network interface, wherein the GPS network interface records location and timestamp information of the portable device, and wherein the memory further comprises instructions for causing the processor to perform the further step of communicating the location and timestamp information to a server.

14. The portable device of claim 1, wherein the user provided information comprises user input received at the input device providing a state of the user.

15. The portable device of claim 1, wherein the device collected information comprises one or more of: a user's heart rate, a user's blood pressure, a users body temperature and a user's blood glucose level.

16. The device of claim 1, wherein the health monitoring mode configures the input device and the one or more sensors to collect diagnostic and health-related information.

17. The device of claim 1., wherein the emergency countdown mode initiates a countdown timer that initiates emergency service contact unless the user enters a personal identification number via the input device.

18. The device of claim 1, wherein the activity duration monitoring mode configures the device to accept input from the user indicating a specific activity and expected duration of that activity.

19. The device of claim 1, wherein the geofence mode configures the device to notify an emergency contact upon the device leaving a predefined geographic boundary.

20. A system for monitoring a user, the system comprising:
a portable device associated with the user; and
a server communicatively coupled to the portable device through a wireless network,
wherein the portable device comprises:
 a processor;
 a network interface for communicating with the wireless network;
 an input device for accepting user provided information of the user of the portable device;
 one or more sensors for collecting device collected information from the user of the portable device;
 a memory comprising instructions for causing the processor to perform the steps of:
  collecting at least one of the user provided information and the device collected information; and
  transmitting, by the network interface over the wireless network, the at least one of the user provided information and the device collected information to the server,
wherein the portable device is configurable to operate in two or more of a plurality of operation modes, the operation modes include: a health monitoring mode, an emergency countdown mode, an activity duration monitoring mode, a location monitoring mode, an emergency contact mode, a geofence mode, a preset notification message mode, and a location tracking mode.

21. The system of claim 20, wherein the server comprises:
a server processor; and
a server memory comprising server instructions for causing the server processor to perform steps of:
 receiving the at least one of the user provided information and the device collected information from the portable device;
 determining whether the at least one of the user provided information and the device collected information acts as a triggering event; and.
 conditionally communicating a notification message to a user contact when it is determined that the at least one of the user provided information and the device collected information acts as the triggering event,
wherein the notification message contains one or more of the user provided information and the device collected information.

22. The system of claim 21, wherein the server memory further comprises server instructions for causing the server processor to perform the further step of storing the at least one of the user provided information and the device collected information at the server.

23. The system of claim 21, wherein the server memory further comprises server instructions for causing the server processor to perform the further step of transmitting to the portable device a user contact status message indicating that the notification message has been communicated to the user contact.

24. A method of reporting a status of a user of a portable device to a user contact, the method comprising:
receiving at least one of user provided information and device collected information of the user collected by at least one of an input device and one or more sensors associated with the portable device;
determining, based on the at least one of the user provided information and the device collected information, whether a triggering event has occurred; and
conditionally communicating the status of the user of the portable device to the user contact when the triggering event has occurred,
wherein the portable device is configurable to operate in two or more of plurality of operation mode, the operation mode include: a health monitoring mode, an emergency countdown mode, an activity duration monitoring mode, a location monitoring mode, an emergency contact mode, a geofence mode, a preset notification message mode, and a location tracking mode.

25. The method of claim 24, further comprising transmitting a user contact status message indicating that the status of the user of the portable device has been communicated to the user contact.

* * * * *